(12) United States Patent
Zhang

(10) Patent No.: US 10,149,863 B2
(45) Date of Patent: Dec. 11, 2018

(54) NKT-LIKE CELL SUBPOPULATION AND METHOD OF USING THE SAME IN THE TREATMENT OF TUMOR

(71) Applicant: Tsinghua University, Beijing (CN)

(72) Inventor: Minghui Zhang, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 0 days.

(21) Appl. No.: 15/231,083

(22) Filed: Aug. 8, 2016

(65) Prior Publication Data

US 2017/0042939 A1    Feb. 16, 2017

(30) Foreign Application Priority Data

Aug. 13, 2015   (CN) .......................... 2015 1 0494011

(51) Int. Cl.
*A61K 35/17* (2015.01)
*C12N 5/0783* (2010.01)
*A61K 35/12* (2015.01)

(52) U.S. Cl.
CPC ............ *A61K 35/17* (2013.01); *C12N 5/0646* (2013.01); *A61K 2035/124* (2013.01); *C12N 2501/22* (2013.01); *C12N 2501/2302* (2013.01); *C12N 2501/2304* (2013.01); *C12N 2501/2305* (2013.01); *C12N 2501/2306* (2013.01); *C12N 2501/2307* (2013.01); *C12N 2501/2309* (2013.01); *C12N 2501/2312* (2013.01); *C12N 2501/2315* (2013.01)

(58) Field of Classification Search
CPC ............................................. C12N 2501/2309
See application file for complete search history.

(56) References Cited

PUBLICATIONS

Zupo et al. J of Clinical Immunology, 1993, 13(3):228-236.*
Baker et al. Blood, 2001, 97(10):2923-2931.*
Godfrey et al. Nature Immunology, 2010, 11(3):197-206.*
Watzl, C. and Long, E. O., "Exposing tumor cells to killer cell attack," Nature Medicine, Aug. 2000, vol. 6, No. 8: pp. 867-868.
Budd, R. C., Miescher, G. C., Howe, R. C., Lees, R. K., Bron, C. and MacDonald, H. R., "Developmentally regulated expression of T cell receptor β chain variable domains in immature thymocytes," J. Exp. Med., Aug. 1987. vol. 166: pp. 577-582.
Fowlkes, B. J., Kruisbeek, A. M., Ton-That, H., Weston, M. A., Coligan, J. E., Schwartz, R. H. and Pardon, D. M., "A novel population of T-cell receptor αβ-bearing thymocytes which predominantly expresses a single $V_\beta$ gene family," Nature, Sep. 17, 1987, vol. 329: pp. 251-254.
Ceredig, R., Lynch, F. and Newman, P., "Phenotypic properties, interleukin 2 production, and developmental origin of a "mature" subpopulation of Lyt-2⁻L3T4⁻ mouse thymocytes." Proc. Natl. Acad. Sci. USA, Dec. 1987, vol. 84: pp. 8578-8582.
Sykes, M., "Unusual T cell populations in adult murine bone marrow. Prevalence of $CD3^+CD4^-CD8^-$ and $\alpha\beta TCR^+NK1.1^+$ cells," Journal of Immunology, Nov. 15, 1990, vol. 145: pp. 3209-3215.
Makino, Y., Kanno, R., Ito, T., Higashino, K. and Taniguchi, M., "Predominant expression of invariant $V_\alpha 14^+$ TCR α chain in NK1.1+T cell populations," International Immunology, Apr. 6, 1995, vol. 7, No. 7: pp. 1157-1161.
Godfrey, D. I., MacDonald, H. R., Kronenberg, M., Smyth, M. J. and Van Kaer, L., "NKT cells: what's in a name?," Nature Reviews/Immunology, Mar. 2004, vol. 4: pp. 231-237.
Maeda, M., Shaded, A., MacFadyen, A. M. and Takei, F., "CD1d-independent NKT cells in $\beta_2$-microglobulin-deficient mice have hybrid phenotype and function of NK and T cells," Journal of Immunology, 2004, vol. 172: pp. 6115-6122.

* cited by examiner

*Primary Examiner* — Bin Shen
(74) *Attorney, Agent, or Firm* — Ladas & Parry, LLP

(57) ABSTRACT

The disclosure discloses a kind of new NKT-like cell subpopulation, a therapeutical composition comprising the NKT-like cell subpopulation, and the medical use thereof. The disclosure also provides a preparation method of the NKT-like cell subpopulation. The disclosed NKT-like cell subpopulation has a strong antitumor effect, and can be adoptive transferred into a subject to treat the tumor in the subject after in vitro cultured and amplified.

14 Claims, 10 Drawing Sheets
(3 of 10 Drawing Sheet(s) Filed in Color)

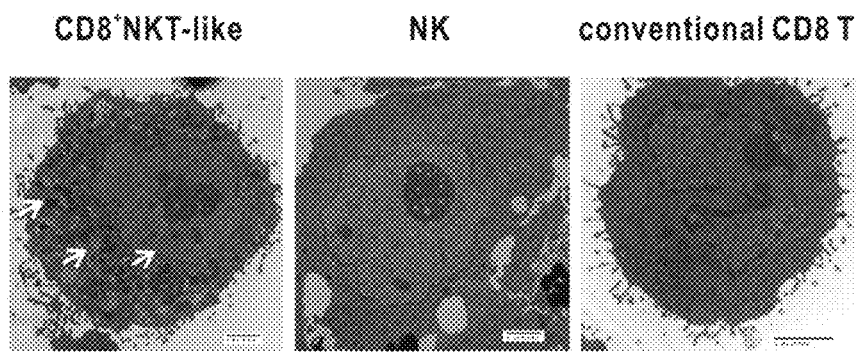
Figure 3A
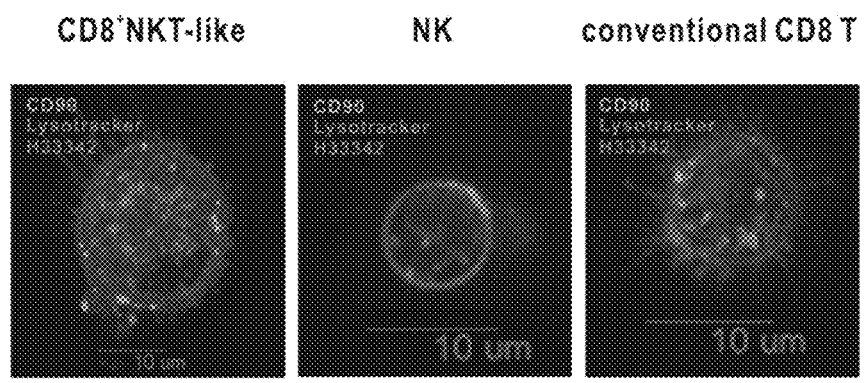
Figure 3B
Figure 3

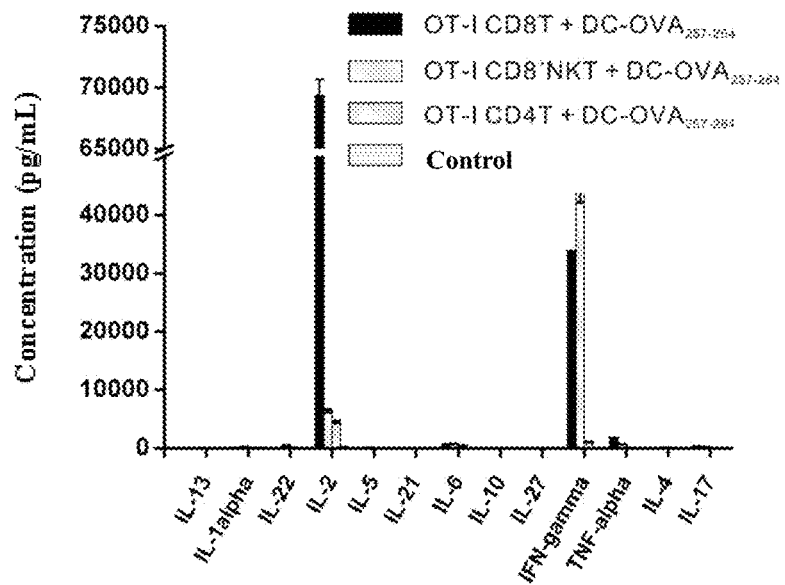
Figure 4A
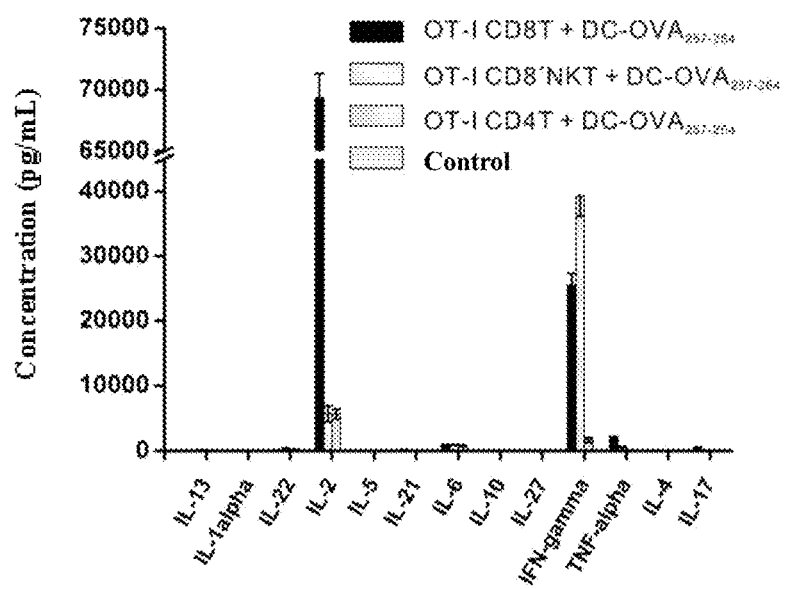
Figure 4B
Figure 4

1. Isolation of human PBMCs

2. Sorting CD8⁺NKT-like cells

3. Amplification of CD8⁺NKT-like cells by addition of cytokines

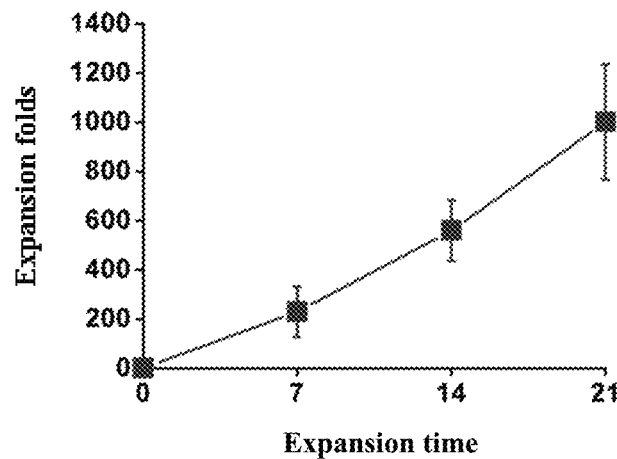
Figure 6A
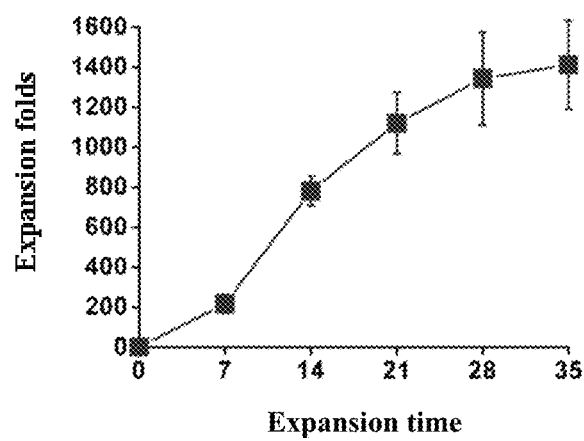
Figure 6B
Figure 6

Control mice

Treated mice

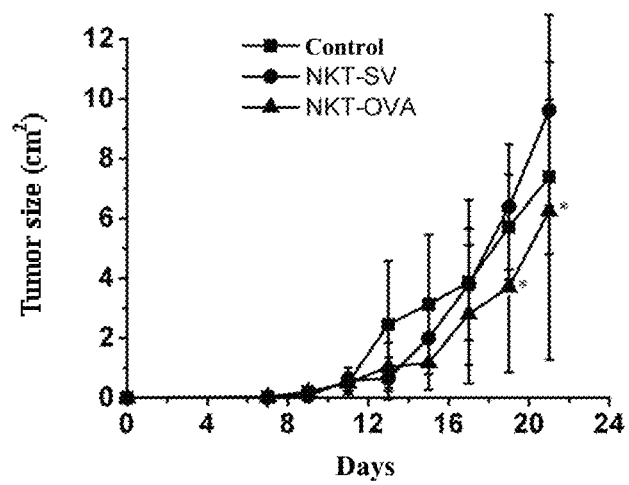
Figure 9A
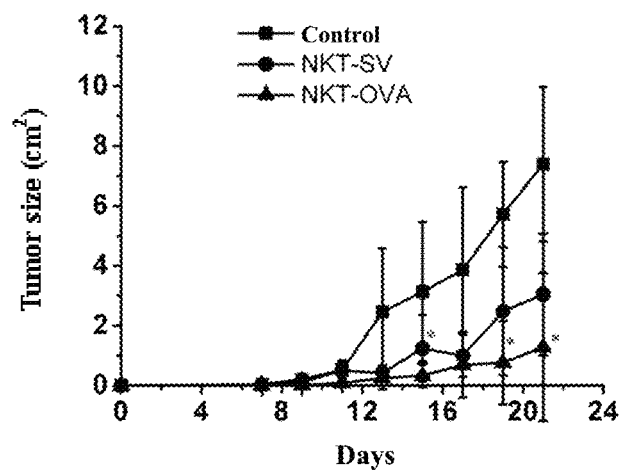
Figure 9B
Figure 9

NKT-LIKE CELL SUBPOPULATION AND METHOD OF USING THE SAME IN THE TREATMENT OF TUMOR

CROSS REFERENCE TO RELATED APPLICATIONS

The present application is based on, and claims priority from CN Application Number 201510494011.4, filed on Aug. 13, 2015, the disclosure of which is incorporated by reference herein in its entirety.

TECHNICAL FIELD

This disclosure relates to a new type of NKT-like immune cell subpopulation. In particular, the NKT-like cell subpopulation comprises CD8$^+$ NKT-like cells. The disclosure also relates to a method of preparing the NKT-like cell subpopulation, a therapeutical composition comprising the CD8$^+$ NKT-like cells and a method of using the NKT-like cell subpopulation or the therapeutic composition in the treatment of tumor.

BACKGROUND

CTL cells and NK cells are known as the major effector cells in the anti-tumor immune response. CTL cells can recognize and kill tumor cells expressing MHC Class I molecules and specific tumor antigens. However, the expressions of MHC Class I molecules are down regulated in many tumor tissues, and in this situation, CTL cells cannot recognize them, while NK cells expressing natural killer cell receptors will act as the main effector cells to kill tumor. NK cells and CTL cells elicit their anti-tumor effects via the binding of the receptors expressed on the surface of their cell membrane to the corresponding ligands on the surface of tumor cells which triggers the release of cytotoxic components from effector cells. Therefore, the discovery of a kind of immune cells expressing both natural killer cell receptors and T cell surface marker TCRβ/CD3, which is also known as NKT cell, has attracted great attentions in the field of immunology.

In 1987, three independent research teams reported a population of T cells expressing a moderate intensity of TCRαβ and having no expressions of CD4 and CD8[2-4], respectively; in 1990, Sykes reported a cell subpopulation which expresses both NK1.1 and TCRαβ[5]. In 1995, "NKT" cell was firstly used as a proper noun, and it especially refers to a subpopulation of T cells expressing NK1.1 (mouse, CD161c) marker[6]. According to the CD1d restriction and the TCR diversity of NKT cells, Godfrey classified mouse NKT cells into three types of populations: Type I NKT cell, Type II NKT cell and NKT-like cell. Type I NKT cell was classified as a population of NKT cells that can recognize CD1d presented α-Galcer lipid antigens, Type II NKT cell can recognize CD1d presented lipid antigens other than α-Galcer, and NKT-like cell includes other NKT cell subpopulations other than Type I NKT cell and Type II NKT cell. Among them, most extensive researches have been made on the immunological features and functions of the Type I NKT cell which is also known as a classical NKT cell; at present, most of NKT cells mentioned in the literatures are actually the classical NKT cells. With the development of CD1d tetramer technology as well as the establishment of CD1d-deficient transgenic mice, the current researches on NKT cells mostly focused on the classical NKT cell (i.e., Type I NKT cell). However, Type I NKT cell is only one population of NKT cell, and more than 50% of NKT cells are NKT-like cells[7].

Type II NKT cells is characterized that its development depends on the CD1d molecule, and yet these cells express relatively diverse TCR chains. The development of NKT-like cell does not depend on CD1d molecules, and yet NKT-like cell expresses a variety of TCR chains. However, there are few researches on the Type II NKT cells and the NKT-like cells at present. Existing researches showed that the Type II NKT cells have some immunomodulating functions, and NKT-like cells have an antitumor effect. A population of NKT-like cells which is not dependent on CD1d molecules has been found in β2 microglobulin deficient mice, and these cells can be able to kill many kinds of tumor cells in vitro[8].

However, the mechanism of the anti-tumor activity of NKT-like cells was still not elucidated based on the results from normal mice up to now. Therefore, there is a need to characterize the subpopulations of NKT-like cell that have an anti-tumor effect and its anti-tumor mechanism, so as to further study the cell subpopulations and the possibility of their clinical application.

SUMMARY

The present inventor has unexpectedly found a NKT-like cell subpopulation having a special phenotype by a large number of basic and applied researches. The cell subpopulation is proved to have a potent anti-tumor ability.

In a first aspect, the disclosure provides an isolated NKT-like cell subpopulation (hereinafter sometimes referred to as "the NKT-like cell(s) of the disclosure" or "the NKT-like cell(s) disclosed herein"). The NKT-like cell subpopulation disclosed therein may comprise NKT cells expressing CD8 molecule on their surface (hereinafter sometimes referred to as "CD8$^+$ NKT-like cell(s) of the disclosure" or "CD8$^+$NKT-like cell(s) disclosed herein").

In an embodiment, the NKT-like cells of the disclosure may comprise a certain proportion of immune cells not expressing CD8 molecule (sometimes referred to herein as "CD8$^-$ immune cells"). The proportion of CD8$^+$NKT-like cells disclosed herein in the NKT-like cells of the disclosure may be 50% or more, preferably 60% or more, more preferably 70% or more, most preferably 80% or more.

In an embodiment, the NKT-like cells of the disclosure may comprise 100% of CD8$^+$ NKT-like cells, that is, all of the NKT-like cells of the disclosure being CD8$^+$ NKT-like cells.

According to some embodiments, the NKT-like cells of the disclosure may be isolated from a mammal.

In a second aspect, the disclosure provides a method of activating and amplifying the NKT-like cells of the disclosure (sometimes referred to herein as "the amplification method of the disclosure"), the method comprising the following steps:

1) collecting peripheral blood from a subject, separating and removing red blood cells from the peripheral blood;

2) isolating mononuclear cells from the peripheral blood obtained in step 1) from which red blood cells have been removed, and sorting the NKT-like cells of the disclosure by using a cell sorting technique known in the art (for example, by means of a cell sorting technique well-known in the art) with the surface markers of the CD8$^+$NKT-like cells (for example, TCRαβ, CD3, CD56/CD161c, CD8, Vα24 TCR or Vα14 TCR, or any combinations thereof);

3) culturing the NKT-like cells of the disclosure obtained in step 2) in vitro, and adding to the culture cytokine(s) that can stimulate the proliferation and activation of T cell for a period of time enough to amplify the number of the NKT-like cells of the disclosure by at least 10~1000 times; and 4) harvesting the NKT-like cells of the disclosure obtained in step 3).

It should be appreciated that in the amplification method of the disclosure, the steps 2) and 3) may be interchangeable, i.e., sorting followed by amplifying, or amplifying followed by sorting. Due to the small amount of the NKT-like cells of the disclosure contained in the peripheral blood, in another preferred embodiment, the amplification method of the disclosure may be performed by firstly amplifying followed by sorting (that is, firstly performing step 3), then step 2)), then sorting the target cells.

In consideration of the convenience in clinical use and reducing the cross infection or iatrogenic infection during the blood collection, the amplified NKT-like cells of the disclosure may be prepared as a therapeutical composition so as to be convenient for storage and for subsequent usage at any time.

Therefore, in a third aspect, the disclosure provides a therapeutical composition comprising the NKT-like cells of the disclosure as a main active ingredient.

In a fourth aspect, the disclosure relates to the use of the NKT-like cells disclosed herein or the therapeutical composition disclosed herein in the preparation of a medicament for the treatment of tumor.

In a fifth aspect, the disclosure provides a method of treating a tumor in a subject in need thereof, the method comprising the following steps:

1) collecting peripheral blood from the subject;

2) isolating mononuclear cells from the peripheral blood of the subject, enriching the NKT-like cells of the disclosure (for example, by using a cell sorting technique known in the art) and amplifying the NKT-like cells in vitro; and 3) harvesting the amplified NKT-like cells of the disclosure obtained in step 2) and then adoptive transferring the amplified cells to the subject.

Due to the small amount of the NKT-like cells of the disclosure in the peripheral blood, in the above-mentioned treatment method, mononuclear cells may be firstly amplified and then NKT-like cells of the disclosure may be enriched.

Some aspects, advantages, and novel features have been described in the above summary. However, it is to be understood that not necessarily all such advantages will be embodied in any particular embodiment of the invention. Therefore, those skilled in the art will appreciate that the present invention can be practiced or performed by means of a combination of one or more advantages as taught herein, and not necessarily achieve other or all advantages as taught or set forth herein.

DESCRIPTION OF DRAWINGS

The patent or application file contains at least one drawing executed in color. Copies of this patent or patent application publication with color drawing(s) will be provided by the Office upon request and payment of the necessary fee.

With reference to the following drawings, the preferred embodiments of the disclosure will be illustrated, and the above and other features, aspects and advantages of the disclosure will be described in more detail. It will be appreciated that the exemplary embodiments are intended to illustrate rather than limit the invention. In the drawings:

In FIG. 1, the black line denotes molecular expression level, and the gray line denotes the expression level of corresponding isotope control.

In FIG. 2, hollow area denotes the expression level of molecules, and the fill area denotes the expression level of corresponding isotope control.

FIG. 3 shows the transmission electron micrographs and the laser confocal micrographs of the mouse CD8$^+$NKT-like cells disclosed herein, mouse NK cells and mouse CD8$^+$T cells, in which FIG. 3A shows transmission electron micrographs, and FIG. 3B shows laser confocal micrographs. In the micrographs of FIG. 3B, red color indicates a positive staining of lysosomal dye LysoTracker, green color indicates a positive staining of FITC-labeled anti-mouse CD90 antibody, and blue color indicates a positive staining of Hoechst33342 dye.

FIG. 4 compares the cytokine secretory abilities of the mouse CD8$^+$NKT-like cells disclosed herein, mouse CD8$^+$T cells and mouse CD4$^+$T cells, in which FIG. 4A shows the result detected at 24 h after antigen challenge, and FIG. 4B shows the result detected at 48 h after antigen challenge.

FIG. 6 are graphs showing the in vitro amplification ability of the CD8$^+$NKT-like cells disclosed herein, in which the expansion folds of the CD8$^+$NKT-like cells at different time points after treated with cytokines are shown. FIG. 6A shows the results obtained from the mouse CD8$^+$NKT-like cells, and FIG. 6B shows the results obtained from the human CD8$^+$NKT-like cells.

FIG. 9 illustrates curves that plot the tumor size against the survival time of the mice inoculated with EL4-OVA8 tumor cells after adoptive transferred with the CD8$^+$NKT-like cells having different antigen specificities. FIG. 9A shows a curve that plots the tumor size of the mice inoculated with EL4-OVA8 tumor cells after adoptive transferred with $2.5 \times 10^5$ CD8$^|$NKT-like cells having different antigen specificities. FIG. 9B shows a curve that plots the tumor size of the mice inoculated with EL4-OVA8 tumor cells after adoptive transferred with $5 \times 10^5$ CD8$^+$NKT-like cells having different antigen specificities.

FIG. 10 is a broken line graph depicting the killing rates of the CD8$^+$NKT-like cells and NK cells on Yac-1 tumor cells at different Effector:Target ratios.

FIG. 11 is a broken line graph depicting the kill rates of the OVA antigen specific CD8$^+$NKT-like cells and OVA antigen specific CD8$^+$T cells on EL4-OVA8 tumor cells.

DETAILED DESCRIPTION

Figure 1:
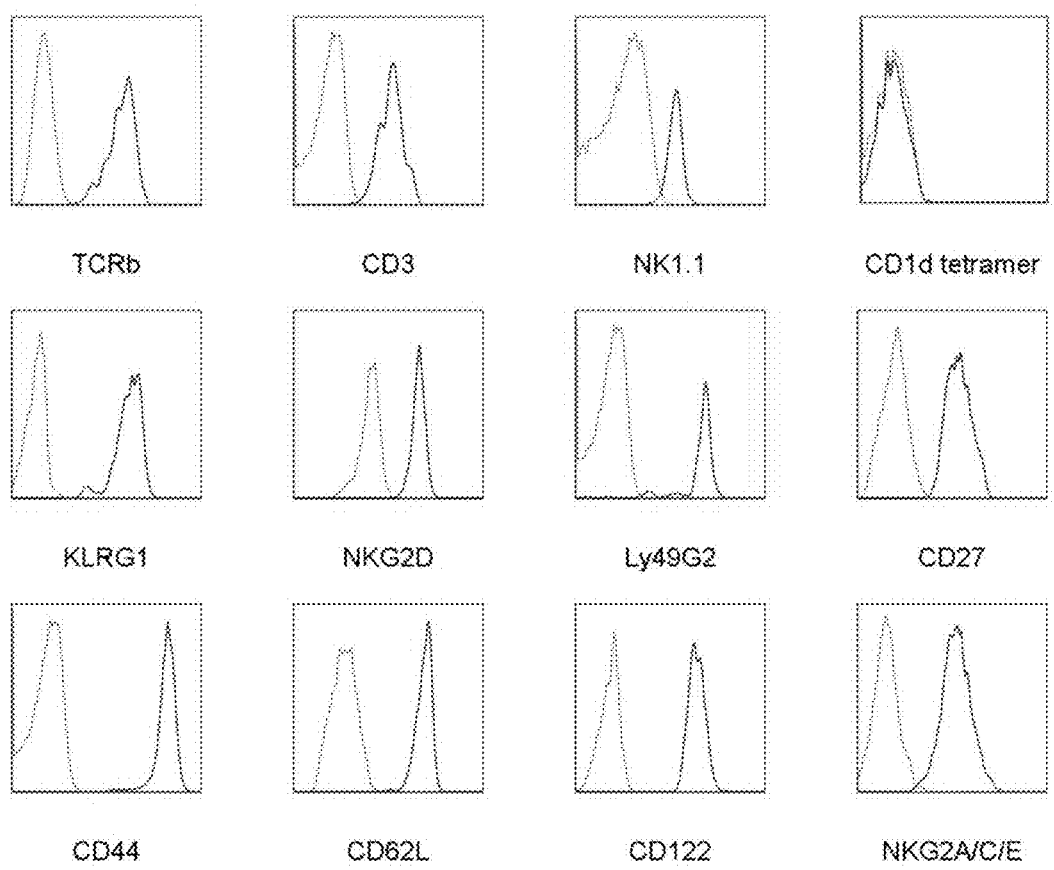
FIG. 1 shows the phenotype of the mouse CD8$^+$NKT-like cells disclosed herein.

Unless defined otherwise, all technical and scientific terms used herein have the same meanings as commonly understood by one of ordinary skill in the art to which this invention belongs. Although any methods and materials similar or equivalent to those described herein can be used in the practice or testing of the invention, the preferred methods, and materials are now described. All publications and patent applications cited herein are incorporated herein by reference in their entirety. Nothing herein is to be construed as an admission that the invention is not entitled to antedate such disclosure by virtue of prior invention.

It must be noted that as used herein and in the appended claims, the singular forms "a," "an," and "the" include plural references unless the context clearly dictates otherwise.

Definitions

As used herein, the term "NKT cell" has two definitions in broad sense and narrow sense. The NKT cell in broad sense refers to a cell population expressing both NK cell surface marker (CD161c in mouse, and CD 56 in human) and T cell surface markers. With the development of lipid antigen bound CD1d tetramer technology, researchers have found a cell subpopulation capable of binding CD1d tetramers loaded with lipid antigen α-GalCer in mice, the majority of cells in the subpopulation expressing both NK cell surface marker and T cell surface markers. Such cell subpopulation secretes a great amount of cytokines and has an immunomodulatory activity; according to Godfrey definition, this population of cells was classified as the type I NKT cell, namely, NKT cell in narrow sense. At present, most extensive and most thorough researches have been made on this population of cells and thus this population of cells is also known as a classical NKT cell. The NKT cell mentioned in literatures mainly is the NKT cell in narrow sense. In the disclosure, unless explicitly specified, the NKT cell refers to the NKT cell in broad sense for all purpose.

As used herein, the term "iNKT cell", namely, NKT cell in narrow sense, is also known as invariant NKT cell (sometimes referred to as iNKT cell herein)[7], owing to the fact that the subpopulation expresses invariant TCR chain (Vα14Jα18 in mouse, Vα24Jα18 in human).

The term "The NKT-like cell" as used herein refers to a cell subpopulation expressing both NK cell surface marker (CD161c in mouse, CD56 in human) and T cell surface markers (for example, TCR and/or CD3) with its development independent on CD1d molecule. This population of cells is characterized that the surface of individual cell may express different types of TCR respectively. However, this population of cells does not include the cells expressing Vα24 TCR (human) or Vα14 TCR (mouse)[7]. The definition of this population of cells is opposed to those of classical NKT cell or NKT cell in narrow sense (in terms of Vα24 TCR or Vα14 TCR).

The term "Vα24 TCR" as used herein refers to TCR sequence that expresses Vα24 gene. According to classical immunology theory, the rearrangement of TCR sequence is considered to result in the diversity of TCR sequence of T cells, while some cell subpopulations having special TCR preferentially express certain type of TCR sequence. For example, the classical NKT cell preferentially expresses Vα24 TCR. The definition of "Vα14 TCR" is similar to that of "Vα24 TCR".

The term "CD1d restricted" as used herein refers to the dependence of development of immune cells on CD1d molecule. In populations of NKT cells, the classical NKT cells are considered to be CD1d restricted, and NKT-like cells are considered to be non-CD1d restricted.

The term "CD8$^+$" as used herein means that CD8 marker is expressed on the cell surface.

The term "CTL cell" as used herein is an abbreviation of Cytotoxic T Lymphocyte, and it refers to a population of effector T cells having a potent ability of killing target virus infected cells formed from T cells expressing CD8 marker (also known as "CD8$^+$ T cell") after antigen specific challenges. It should be noted that the concept of classical CTL cells does not cover the NKT cells expressing NK cell marker (CD56) and NKT-like cells expressing NK cell marker (CD56).

NKT-Like Cells of the Disclosure

The disclosure discloses a NKT-like cell subpopulation comprising NKT-like cells expressing CD8 molecules.

In an embodiment, the NKT-like cells of the disclosure may comprise a certain proportion of immune cells not expressing CD8 molecule. The proportion of CD8$^+$NKT-like cells disclosed herein in the NKT-like cells of the disclosure may be 50% or more, preferably 60% or more, more preferably 70% or more, most preferably 80% or more.

Preferably, the NKT-like cells of the disclosure may comprise 100% of CD8$^+$ NKT-like cells, that is, all of the NKT-like cells of the disclosure being CD8$^+$ NKT-like cells.

According to some embodiments, the CD8$^+$ NKT-like cells disclosed herein may express CD3 and CD56 (or CD161c), but not Vα24 TCR(Vα14 TCR), namely that, its phenotype may be denoted as CD3$^+$CD56$^+$CD8$^+$Vα24 TCR$^-$ or CD3$^+$CD161c$^+$CD8$^+$Vα14 TCR$^-$.

In a specific embodiment, the surface of the CD8$^+$ NKT-like cells disclosed herein may also express TCRαβ, that is, its phenotype may be denoted as TCRαβ$^+$CD3$^+$CD56$^+$CD8$^+$ Vα24 TCR$^-$ or TCRαβ$^+$CD3$^+$CD161c$^+$CD8$^+$Vα14 TCR$^-$.

FIG. 1 illustrates the phenotype of the CD8$^+$ NKT-like cells disclosed herein. In FIG. 1, it can be seen that the mouse CD8$^+$ NKT-like cells express T cell lineage marker CD3 and TCRβ as well as NK cell lineage marker NK1.1 (CD161c), but do not express iNKT lineage marker CD1d. In addition, it also can be seen from FIG. 1 that the CD8$^+$ NKT-like cells express T cell activation markers (CD44, CD62L and CD122) as well as NK cell receptors (NKG2A/C/E, KLRG1, NKG2D, Ly49G$_2$ and CD27). These results indicate that these cells have the functional characteristics of both NK cells and T cells.

Figure 2:
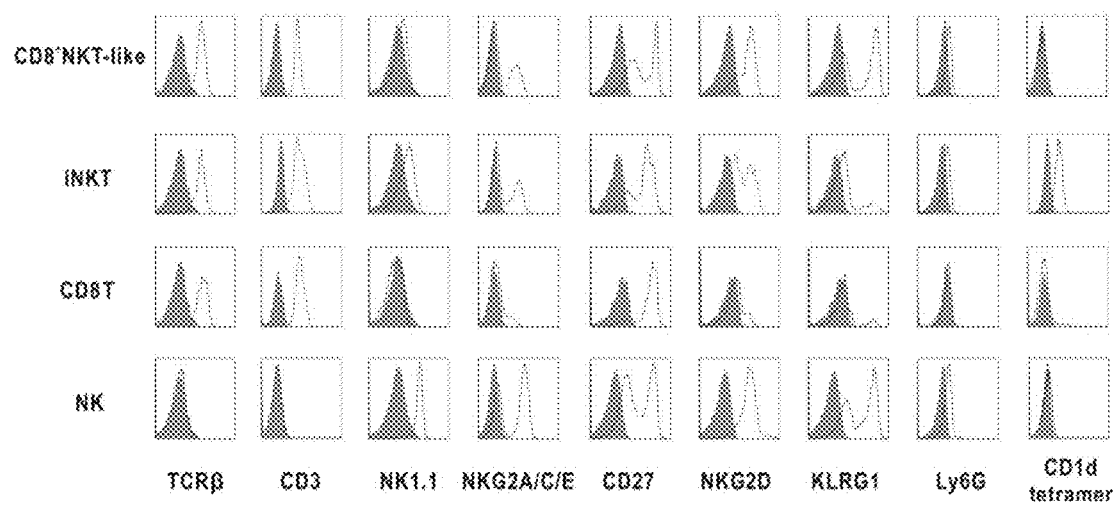
FIG. 2 shows phenotypic differences between the mouse CD8$^+$NKT-like cells disclosed herein and mouse NK cells, mouse iNKT cells and mouse CTL cells.

FIG. 2 shows phenotypic differences between the CD8$^+$ NKT-like cells disclosed herein and NK cells, iNKT cells and CTL cells. It can be seen from FIG. 2 that: (1) compared with NK cells, the mouse CD8$^+$NKT-like cells express not only NK cell markers [NK1.1 (CD161c), NKG2A/C/E, CD27, KLRG1 and Ly6G], but also TCRβ and CD3 which are not expressed on the NK cells; (2) compared with CTL cells, the mouse CD8$^+$NKT-like cells express T cell lineage markers (TCRβ and CD3), but do not express NK cell receptors; (3) compared with iNKT cells, the CD8$^+$NKT-like cells cannot bind to the CD1d tetramer loaded with lipid antigens. These results indicate that the CD8$^+$NKT-like cell disclosed herein is a new immune cell subpopulation which is distinct from any one of the existing immune cell subpopulations having defined phenotypes that were found to have anti-tumor effects in the prior art.

FIG. 3 shows the transmission electron micrographs and the laser confocal micrographs of the CD8$^+$NKT-like cells disclosed herein, NK cells and CD8$^+$T cells. The transmission electron micrographs of FIG. 3A show that the mouse CD8+NKT-like cells disclosed herein contain a large amount of granular substances, while the NK cells and CD8+ T cells contain less similar granular substances. The laser confocal micrographs of FIG. 3B show that the volume of CD8+NKT-like cells disclosed herein is larger and its diameter is more than about 15 μm, while the diameters of NK cells and CD8+ T cells are less than 10 μm, being about 7 μm. At the same time, the granular substance in the CD8+NKT-like cells is positive for lysosomal dye staining, suggesting that the granular substance may contain granzyme that elicits a cytotoxic effect, while NK cells and CD8+ T cells contain less granules that are positive for lysosomal dye staining. In addition, the staining of the nucleus and cell membrane shows that the nuclear-cytoplasmic ratio of the CD8+NKT-like cells is smaller than that of other two kinds of cells. The above morphological differences suggest that the CD8+NKT-like cell is a new and unique immune cell subpopulation which is completely different from NK cells and CD8+ T cells. Moreover, it can be expected from the morphological differences that there are great differences between the functions of the CD8+NKT-like cells and the other two kinds of cells. Intracellular granules which are positive for lysosomal dye staining suggested that the CD8+NKT-like cells disclosed herein may elicit a cytotoxic effect mediated by Granzyme.

FIG. 4 compares the cytokine secretory abilities of the CD8+NKT-like cells disclosed herein, CD8+T cells and CD4+T cells. It can be seen from FIG. 4 that at 24 h and 48 h after specific antigen challenge, IFN-γ level secreted by the mouse CD8+NKT-like cells is obviously higher than those of the CD8+ T cells and the CD4+ T cells; IL-2 level secreted by the CD8+NKT-like cells is lower than that of the CD8+ T cells, but is comparative with that of the CD4+ T cells. In terms of cytokines expression profile, relative to the CD4+ T cells, the expression levels of both IFN-γ and IL-2 are higher in the CD8+ T cells, but only the expression level of IFN-γ is higher in the CD8+NKT-like cells disclosed herein. Therefore, the above results demonstrate that the CD8+NKT-like cells disclosed herein have a unique cytokines expression profile.

In addition, in consideration of the activation efficiency of stimulating T cells and increasing the total number of cells (because of the small content of the NKT-like cell subpopulation of the disclosure in the blood) in order to extend the half-life of cells in blood after back transfusion, the NKT-like cells of the disclosure may contain a certain proportion of CD8− immune cells. In this case, the NKT-like cells of the disclosure may comprise 50%, 60%, 70%, 80%, 90%, 91%, 92%, 93%, 94%, 95%, 96%, 97%, 98%, 99% or more, preferably 60% or more, more preferably 70% or more, most preferably 80% or more of the CD8+ NKT-like cells.

Method for Amplifying the NKT-Like of the Disclosure

The disclosure further provides a method for amplifying the NKT-like cells disclosed herein.

In the disclosure, the mammal may be selected from the species such as bovidae, equidae, felidae, canidae, leporidae, suidae, camelidae, rodent and primate, including but not limited to, a cattle, a horse, a goat, a sheep, a cat, a rabbit, a pig, a camel, an alpaca, a rat, a mouse, a guinea pig and a non-human primate (such as ape, monkey, baboon, orangutan) or a human, preferably a cattle, a horse, a dog, a goat, a sheep, a pig, a camel, a rat, a mouse, a monkey or a human, more preferably a human.

The mammal as used herein may be a pet animal, including but not limited to a pet dog, a pet cat, a pet rodent (for example chinchilla, hamster, white mouse, gerbil, chipmunk, octodont, squirrel, flying squirrel and big *Tamias sibiricus*, etc.), a pet rabbit, a mink, a hedgehog, an alpaca, a guinea pig, a cattle, a monkey, a sheep, a pig, a horse, a deer, an elephant, a rhinoceros, etc., preferably a pet dog, a pet cat, a monkey, a sheep, and the like.

Unless specifically indicated, the above description and definition of mammal is applicable to all sections, paragraphs, any one embodiment, examples and claims that recite the mammal herein.

In the amplification method of the disclosure, the methods of collecting peripheral blood and isolating mononuclear cells are not particularly limited, and the methods well-known in the art, for example, a method in which a method or an equipment of extracorporeal circulation (for example, a mononuclear cell separator, circulating 3000~6000 mL of peripheral blood) is used, may be employed.

In the amplification method of the disclosure, the method of removing red blood cells from anticoagulated blood is not particularly limited, and the methods well-known in the art, for example, a method of density gradient centrifugation, may be employed.

The cell sorting technique used in the amplification method of the disclosure is well-known in the art, and can be accomplished by using the method or equipment commonly used in the art, without any limitation in the disclosure. Any technologies, methods and equipments to sort cells may be used in the disclosure, as long as the surface markers are used to sort cells in these technologies, methods and equipments. For example, a magnetic sorting technique or a flow cytometry can be used. The experimental processes of the cell sorting technique such as a magnetic separation technique or a flow cytometry can be found in various scientific literatures, or may be performed according to instructions or recommended protocols provided by the manufacturer of the equipment or instrument. A person skilled in the art would have the ability to obtain these specific experimental processes or protocols.

With regard to the surface markers, a single marker or a combination of two or more markers may be selected according to the species of the subject (e.g., human, mouse, dog, etc.) and the range of the proportion of target cells to be isolated and enriched in the final isolated cells (e.g., 50%, 60%, 70%, 80%, 90% or more). For example, a combination of CD3, CD56, CD8 and Vα24 TCR may be selected for human NKT-like cells, and a combination of CD3, CD56, CD8, Vα24 TCR and TCRαβ (that is, sorting out TCRαβ+CD3+CD56+CD8+Vα24 TCR−NKT-like cells) is used so as to obtain a higher enrichment ratio by adding a marker, TCRαβ to the combination. Furthermore, a combination of CD3, CD161c, CD8 and Vα14 TCR may be selected for mouse NKT-like cells, and a combination of CD3, CD161c, CD8, Vα14 TCR and TCRαβ (that is, sorting out TCRαβ+CD3+CD161c+CD8+Vα14 TCR−NKT-like cells) is used so as to obtain a higher enrichment ratio by adding a marker, TCRαβ to the combination.

The culture condition of the NKT-like cells of the disclosure is not particularly limited in the amplification method of the disclosure. Culture media routinely used for T cell culture, such as RPMI-1640 culture medium, may be employed. The conditions commonly used for culturing T cells may be employed, for example, at 37° C., 5% $CO_2$, and changing culture medium every 3 to 5 days. The amplification and activation of the NKT-like cells of the disclosure may be achieved by adding some cytokines, for example, the cytokines that can be able to stimulate T cell proliferation and activation, including but not limited to, GM-CSF, IL-2, IL-4, IL-5, IL-6, IL-7, IL-9, IL-12, IL-15 and 4-1BBL, and the like, to the culture.

A person skilled in the art may specifically determine the culture time according to the use of the amplified cells. The cells may be sampled regularly and be subjected to cell count so as to estimate the number of amplified cells or the expansion folds of cells, thereby controlling the culture time according to the results. In the clinical use, the amount of self-transfused cells in the adoptive transfer of human immune cells may be $1\times10^9 \sim 1\times10^{12}$ cells, preferably $1 \sim 10\times 10^{10}$ cells. In the adoptive transfer of mouse immune cells, the amount of self-transfused cells may be $1 \sim 100 \times 10^6$ cells. Generally, the culture time should be enough to expand the number of initially isolated cells or sorted cells by 10~1000 times, typically for 7~30 days, preferably 10~27 days, preferably 14~21 days.

A specific embodiment of the amplification method of the NKT-like cells of the disclosure may comprise the following steps:

1) collecting peripheral blood of a subject to an anticoagulation tube, then removing red blood cells by density gradient centrifugation;

2) isolating mononuclear cells from the peripheral blood from which red blood cells have been removed, and sorting $CD3^+CD56^+CD8^+V\alpha24\ TCR^-$ (and optionally $TCR\alpha\beta^+$ $CD3^+CD56^+CD8^+V\alpha24\ TCR^-$) NKT-like cells by means of a flow cytometry with surface markers CD3, CD56 (in the case that the subject is human) or CD161c (in the case that the subject is mouse), CD8, $V\alpha24$ TCR (in the case that the subject is human) or $V\alpha14$ TCR (in the case that the subject is mouse) and optional $TCR\alpha\beta$;

3) culturing the NKT-like cells of the disclosure obtained in step 2) in vitro in complete medium at 37° C., 5% $CO_2$, and adding to the culture one cytokine or a combination of two or more cytokines selected from the group comprising GM-CSF, IL-2, IL-4, IL-5, IL-6, IL-7, IL-9, IL-12, IL-15 and 4-1BBL for a period of time enough to expand the amount of the NKT-like cells by at least 10~1000 times (the culture time being about 7~30 days, preferably 10~27 days, more preferably 14-21 days, during which the cells are regularly sampled to estimate the number of the cells by cell counting); and 4) harvesting the NKT-like cells of the disclosure obtained in step 3).

Figure 5:
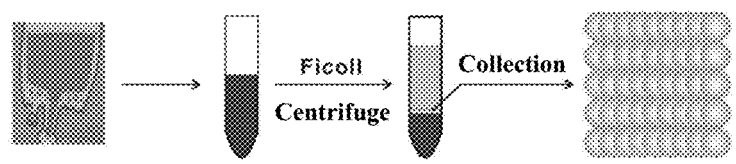
FIG. 5 schematically shows a flow chart of an embodiment of the method of in vitro amplifying the CD8$^+$NKT-like cells disclosed herein.
Figure 5:
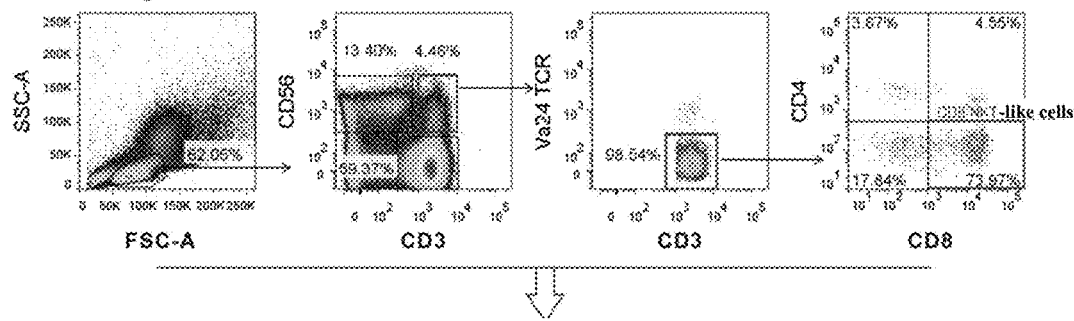
Figure 5:

As a non-limiting example, FIG. 5 schematically shows a flow chart of a specific embodiment of the method of amplifying the NKT-like cells of the disclosure. In the specific example shown in FIG. 5, the mononuclear cells were collected from the peripheral blood by Ficoll centrifugation, and then the $CD8^+$NKT-like cell subpopulation was sorted out by means of a flow cytometer, followed by the amplification of the sorted cells by adding a combination of cytokines (that is, a scheme of firstly sorting and subsequently amplifying).

FIG. 6 illustrates the in vitro amplification ability of the $CD8^+$NKT-like cells disclosed herein. It can be seen from FIG. 6A that the number of the $CD8^+$NKT-like cells increased by more than 1000 times at 21 days of in vitro culture of mouse $CD8^+$NKT-like cells. Since the cell number at 30 days is enough to meet the requirement for self-transfusion, the expansion time for mouse cells may be selected from 7 to 30 days, preferably 10 to 21 days.

In addition, it can been seen from FIG. 6B that the number of human $CD8^+$NKT-like cells increased by 782 times at 14 day, after that the growth rate of the cells tended to slow down and increased by 1120 times at 21 days. Considering the potential tumorigenicity of cells in vitro and the coordination with clinical treatment regimen, the cell culture time should not be too long. Therefore, in clinical application, the cell culture time may be selected from 7 to 30 days, preferably 10 to 27 days, more preferably 14 to 21 days.

The Therapeutical Composition of the Disclosure

As described above, the NKT-like cells of the disclosure may be prepared as a therapeutical composition in order to be convenient for long-term storage and for subsequent usage at any time, thereby not only reducing the times of blood collection of the subject to alleviate the pain and expense of the subject and but also reducing medical operations to lessen the chance of cross infections and iatrogenic infections.

According to some embodiments, the therapeutical composition of the disclosure comprises the NKT-like cells of the disclosure as a main active ingredient. The main active ingredient as used herein refers to an ingredient capable of bringing about a target effect. In the disclosure, the target effect is an anti-tumor effect when the therapeutical composition of the disclosure is used in the treatment of the tumor, and thus the main active ingredient refers to the ingredient of the therapeutical composition that can bring about an anti-tumor effect.

The main active ingredient as used herein refers to a cell component that brings about a target effect when the therapeutical composition of the disclosure is in a form of a cell preparation comprising therapeutical cells. When the therapeutical composition of the disclosure is in a composition form comprising cells and a biomolecule (for example, a protein or a polypeptide, a peptide, a nucleic acid, an antibody, an amino acid, etc.) and/or a chemical (for example, a chemical synthetic drug) which has a certain therapeutic use, the main active ingredient as used herein refers to a combination of a cell component that brings about a target effect and the biomolecule and/or the chemical. Preferably, the biomolecule and/or the chemical may have the same therapeutic use as that of the cells, for example, for use in the anti-tumor treatment. The therapeutic use of the biomolecule and/or the chemical may be different from that of the cells. For example, when the therapeutical cells comprised in the therapeutical composition of the disclosure are used in the anti-tumor treatment, the biomolecule and/or the chemical may be a molecule or a drug having an activity of antagonizing the adverse reactions or side effects of cell therapy, tumor complications or comorbidities (for example, fever, chill, anxiety; ascites, nausea, vomit, abdominal distension, diarrhea, obstruction, heart failure, arrhythmia, dry cough, cough, dyspnea, oliguria, diuresis, proteinuria, hematuresis, pain, skin allergy, skin erythema, cutaneous pruritus, etc.).

When the therapeutical composition of the disclosure is in a form of cell preparation, the NKT-like cells of the disclosure accounts for 50%, 60%, 70%, 80%, 90% or 95% or more (by the number of cells) of the total cells of the therapeutical composition disclosed herein, even 100%, preferably 60% or more, more preferably 80% or more, most preferably 90% or more.

When the therapeutical composition of the disclosure is a composition comprising therapeutical cells and a therapeutical biomolecule and/or a chemical medicament, either in a form of mixture or in a form of separately individual packages (the form of the combination is not limited in any way in the disclosure), the NKT-like cells of the disclosure accounts for 50%, 60%, 70%, 80%, 90% or 95% or more (by weight) of the main active ingredients of the therapeutical composition disclosed herein (namely, the total amount of the cells and the biomolecule and/or the chemical medicament), even 100%, preferably 60% or more, more preferably 80% or more, most preferably 90% or more.

In a preferable embodiment, the therapeutical composition disclosed herein may also comprise pharmaceutical acceptable or physiological acceptable pharmaceutical adjuvants, carriers, stabilizers, diluents, excipients, buffers, isotonic agents and/or additives, etc.

In a further preferable embodiment, the therapeutical composition disclosed herein may also comprise an antifreezing liquid routinely used in the cryopreservation of T cells (for example, CELLBANKER series cell cryopreservation medium, ZENOAQ Co. LTD.), such that the composition can be cryopreserved (below −80° C., e.g., cryopreserved in liquid nitrogen) for a long time.

Medical Uses of the NKT-Like Cells of the Disclosure

By extensive researches, the present inventor has unexpectedly found that the NKT-like cells of the disclosure have a surprisingly powerful anti-tumor effect. The anti-tumor effect is proved to be both in a specific manner and in a non-specific manner, thereby imparting the NKT-like cells of the disclosure a broad anti-tumor profile.

Although there had been some reports in the prior art that suggested the anti-tumor effect of NKT-like cells, the researches on the anti-tumor effect of NKT-like cells in the prior art was still in a preliminary stage at present due to the scarce researches on the NKT-like cells. The overall understanding of the NKT-like cells, such as the teachings about the composition of the subpopulations of NKT-like cells, the phenotype of the respective subpopulations, the intensity of the anti-tumor effect, the anti-tumor profile, and specific anti-tumor mechanism, is still absent.

In particular, the inventor has found through researches that the anti-tumor effect of the NKT-like cells of the disclosure may depend on two mechanisms, in an antigen-specific manner and in a non-antigen-specific manner. This is surprising, because the prior art suggested none of the following hints: the anti-tumor effect of the NKT-like cells is derived from a certain cell subpopulation having specific surface markers, and NKT-like cells or a subpopulation of the NKT-like cells possess a bidirectional anti-tumor effect involving antigen-specific and non-antigen-specific mechanisms. Further from the experimental results, the NKT-like cell of the disclosure has not only a stronger anti-tumor effect, but also a broader antitumor profile, overwhelming the anti-tumor profiles of other immune cell therapies such as CAR-T and CIK.

Figure 7:
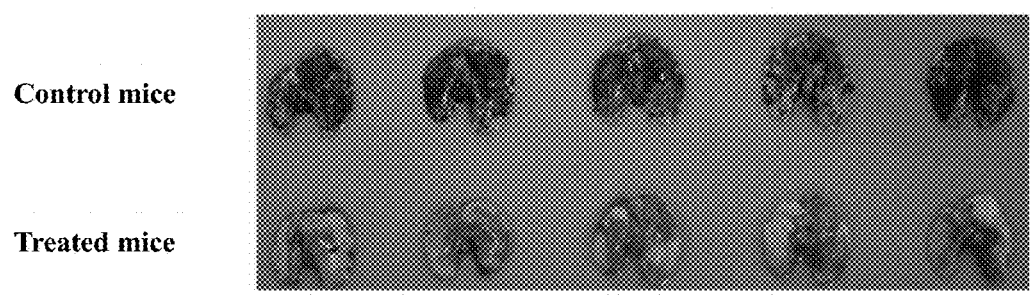
FIG. 7 is a photograph of lung tissues obtained from mice that had been inoculated with B16 melanoma cells via tail vein at 21 days after the CD8$^+$NKT-like cells disclosed herein or PBS control were adoptive transferred to the mice.

In the experiment shown in FIG. 7, the CD8$^+$NKT-like cells disclosed herein or PBS control, were adoptive transferred into mice inoculated with B16 melanoma cells via tail vein. It can be seen from FIG. 7 that melanoma metastases spread all over the lungs of the mice injected with PBS, while the number of the metastases was significantly reduced after the adoptive transfer of the CD8$^+$NKT-like cells. The numbers of the metastases in different groups and the statistical results (by t-test) were summarized in the following table 1.

TABLE 1

| Groups | The number of metastases | Significance test (compared with the control group) |
|---|---|---|
| PBS control | 96 ± 24 | |
| 5 × 10$^6$ CD8$^+$NKT-like cells | 5 ± 7 | P < 0.01 |

Figure 8:
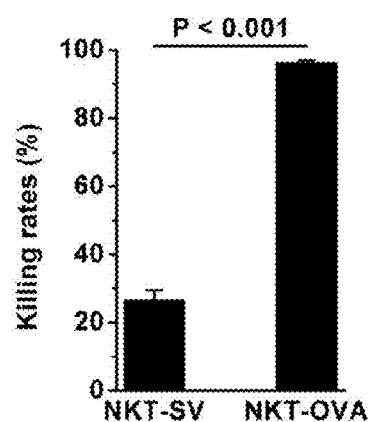
FIG. 8 is a graph illustrating the in vitro antigen-specific killing effects of the mouse CD8$^|$NKT-like cells having different antigen specificities on EL4-OVA8 tumor cells.

FIG. 8 compares the in vitro antigen-specific killing effects of the mouse CD8$^+$NKT-like cells having different antigen specificities on EL4-OVA8 tumor cells. In this experiment, CD8$^+$NKT-like cells isolated from OT-I mice and SV mice (these two populations of cells have antigen specificities on OVA and SV respectively) were co-cultured with the CD8$^|$NKT-like cells in vitro. The results showed that the killing effect of the CD8$^+$NKT-like cells having OVA antigen specificity on EL4-OVA8 tumor cells was much higher than the killing effect of the CD8$^+$NKT-like cells having SV antigen specificity, suggesting that the killing effect of the CD8$^+$NKT-like cells of the disclosure on tumor cells may have some antigen selectivity (i.e., eliciting a specific killing effect via certain antigen(s)) rather than via only non-antigen-specific killing pathway.

FIG. 9 shows the influence of different doses of CD8$^|$NKT-like cells having different antigen specificities on the tumor size and the survival time of the mice. FIG. 9A shows the result of adoptive transferring 5×10$^5$ cells; FIG. 9B shows the result of adoptive transferring 2.5×10$^5$ cells. The result of FIG. 9A showed that since 19 days after transfusion, the volume of EL4-OVA8 tumor in the mice adoptive transferred with OVA specific CD8$^+$NKT-like cells was significantly smaller than the tumor volume of the mice adoptive transferred with SVEL4-OVA8 tumor cells. The similar trend was also observed in the high dose group (FIG. 9B). From FIG. 9B, it can also be seen that OVA antigen specific CD8$^+$NKT-like cells in high dose may even completely inhibit tumor growth. Meanwhile, SV antigen-specific CD8$^+$NKT-like cells showed an anti-tumor effect to some extent (p<0.05). In combination with the result shown in FIG. 9A that SV antigen-specific CD8$^+$NKT-like cells have no significant effect on the tumor volume and the survival time, this result highly suggests that at above a certain dose, the CD8$^+$NKT-like cells disclosed herein can kill tumor cells via both the antigen-specific and the non-antigen-specific pathways, and the killing effect via the antigen-specific pathway may be achieved at a lower dose.

Figure 10:
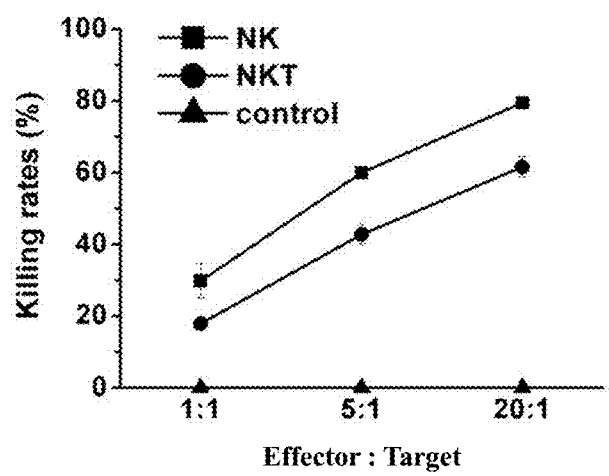
FIG. 10 compares the non-antigen specific killing effects of the CD8$^+$NKT-like cells disclosed herein and NK cells on Yac-1 tumor cells.

FIG. 10 compares the non-antigen-specific killing effects of the CD8$^+$NKT-like cells and NK cells on Yac-1 tumor cells at different Effector:Target ratios (1:1, 5:1 and 20:1, respectively). The result of FIG. 10 indicates that both the CD8$^+$NKT-like cells and the NK cells at different Effector:Target ratios have nonspecific killing effects on Yac-1 tumor cells, and the killing effect of the NK cells is stronger than the CD8$^+$NKT-like cells.

Figure 11:
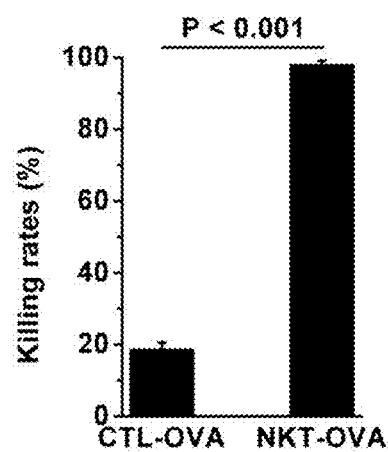
FIG. 11 compares the killing effects of OVA antigen specific CD8$^+$NKT-like cells and OVA antigen specific CD8$^+$T cells on EL4-OVA8 tumor cells.

FIG. 11 compares the killing effects of OVA antigen specific CD8$^+$NKT-like cells and OVA antigen specific CD8$^+$T cells on EL4-OVA8 tumor cells. The result of FIG. 11 indicates that the killing effect of the OVA antigen specific CD8$^+$NKT-like cells is significantly stronger than the OVA antigen specific CD8$^+$T cells.

Figure 12:
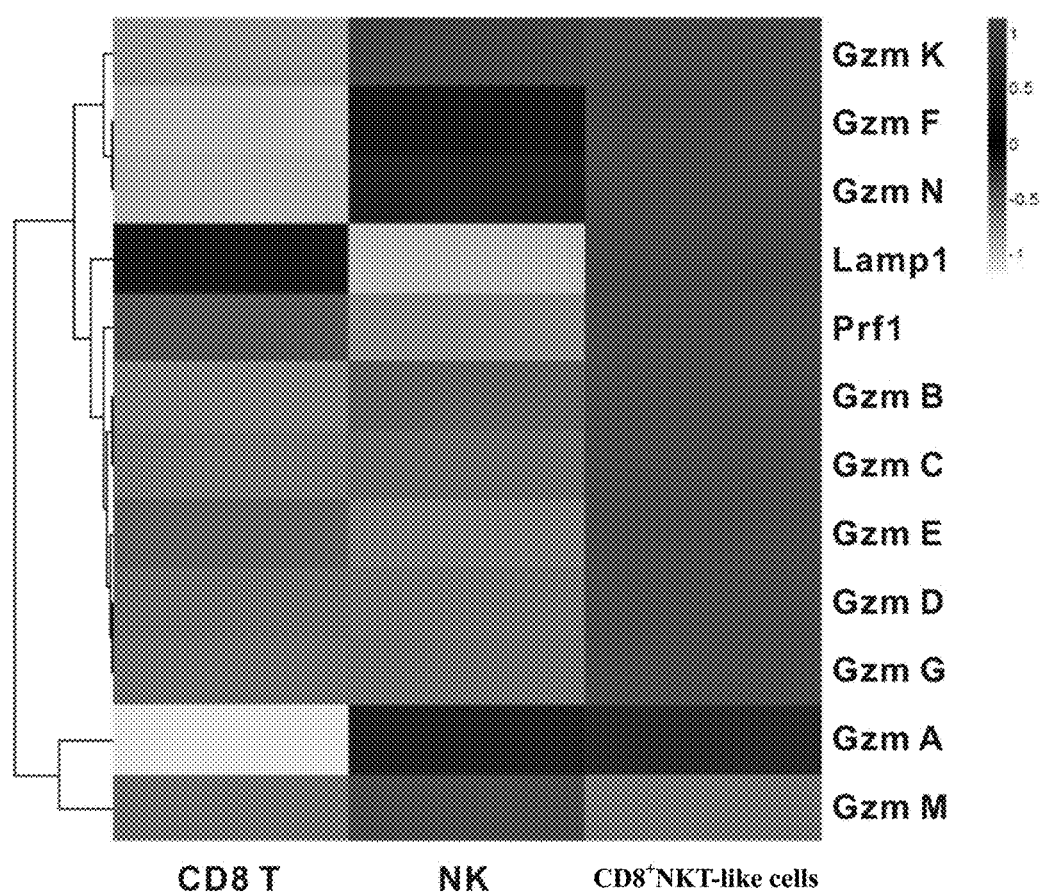
FIG. 12 shows a thermal map depicting the expressions of various Granzymes, Perforin and Lamp-1 on the CD8$^+$NKT-like cells disclosed herein, NK cells and CD8 T cells. There is a color gradation in the upper right of the Figure, and the colors from yellow to red indicate the expression intensities from low to high.

FIG. 12 shows a thermal map depicting the expressions of various Granzymes, Perforin and Lamp-1 on the CD8$^+$NKT-like cells, NK cells and CD8 T cells. The results show that the expression levels of proteins including Granzymes, Perforin and Lamp-1 (CD107a) which are associated with Granzyme release pathway on mouse CD8$^+$NKT-like cells, are significantly stronger than those of NK cells and CD8$^+$ T cells (except for protein Gzmm, protein Gza). The results indicate that the killing effect of the CD8$^+$NKT-like cells disclosed herein on tumor cells may be achieved via the Granzyme release pathway.

Therefore, the CD8$^+$NKT-like cells may have both the ability of NK cells to recognize and kill tumor cells in a non-antigen-specific manner and the ability of CTL cells to recognize and kill tumor cells in an antigen-specific manner. These two abilities may act in a dose dependent manner.

Therefore, the CD8+NKT-like cells of the disclosure can be used in the treatment of tumors. In an embodiment, the tumor may be selected from solid tumors and hematological neoplasms. Solid tumors include but not limited to, gastric cancer, esophageal cancer, small intestine cancer, colorectal cancer, colon cancer, rectal cancer, anal cancer, liver cancer, gallbladder cancer, breast 1.0 cancer, ovarian cancer, cervical cancer, uterine cancer, pancreatic cancer, lung cancer, pharyngeal cancer, laryngeal cancer, nasopharyngeal cancer, thymoma, melanoma, testicular cancer, sarcoma, prostate cancer, metastatic cancer, renal cancer, melanoma, etc. Hematological neoplasms include but not limited to, myeloid malignancies, lymphatic malignancies, malignant histiocytosis and mast cell leukemia, wherein the myeloid malignancies include but not limited to myeloproliferative disorders (MPD), myelodysplastic syndrome (MDS), myelodysplastic/myeloproliferative disorders (MD/MPD) and acute myeloid leukemia (AML); the lymphatic malignancies include but not limited to T/NK cell tumor, B cell tumor and Hodgkin's disease.

Method of Treating Tumor by Using the NKT-Like Cells of the Disclosure

The disclosure provides a method of treating a tumor in a subject in need thereof (sometimes referred to herein as "the therapeutic method of the disclosure"), the method comprising the following steps:

1) collecting peripheral blood from the subject;
2) isolating mononuclear cells from the peripheral blood of the subject, enriching the NKT-like cells of the disclosure and in vitro culturing the NKT-like cells so as to amplify the cell number to $1\times10^9 \sim 1\times10^{12}$ cells; and
3) harvesting the amplified NKT-like cells of the disclosure obtained in step 2) and then adoptive transferring the amplified cells to the subject.

As described above, although in step 2) of the therapeutic method of the disclosure, a scheme of amplifying after enriching (for example, by using a cell sorting) is employed, a scheme of enriching after amplifying may be also employed and the disclosure is not particularly limited thereto. Due to the small amount of the NKT-like cells of the disclosure contained in the peripheral blood, in a preferred embodiment, the enriching step may be performed after the mononuclear cells are expanded to a certain amount, and then the enriched NKT-like cells of the disclosure are adoptive transferred, or optionally the enriched NKT-like cells are further expanded to the desired amount according to the required cell number and then adoptive transferred.

In the therapeutic method of the disclosure, the number of adoptive transferred cells may be $1\times10^9 \sim 1\times10^{12}$ cells, preferably $1\sim10\times10^{10}$ cells for human clinical application. If in mice, the number of adoptive transferred cells may be $1\sim100\times10^6$ cells. If the number of adoptive transferred cells is too large (e.g. more than $1\times10^8$ cells), an immune hyperactivation may be caused, thereby inducing an autoimmune disease. If the number of adoptive transferred cells is too small (e.g. less than $1\times10^6$ cells), the expected therapeutical effect would not be achieved.

In a preferable embodiment, after harvesting cells in step 2), the harvested cells may be prepared as the therapeutical composition disclosed herein and stored for further usage so as to reduce the times of blood collection of the subject and lessen the chance of iatrogenic infections, as described above. In this situation, the therapeutical composition disclosed herein would be transfused into the subject in the step 3).

In the disclosure, the term "treatment" refers to administrate the NKT-like cells of the disclosure or the therapeutical composition of the disclosure to a subject in need thereof so as to obtain any one or more beneficial effects selected from the group comprising the following: reducing the size of tumor, preventing recurrence or metastasis, improving the quality of life of the subject, alleviating or mitigating one or more symptoms or complications associated with tumor, or prolonging the survival time of the subject although the size of tumor is not reduced.

In a preferable embodiment, the modes of transfusion include but not limited to, intravenous infusion, peritoneal perfusion and direct intratumoral injection.

In another preferable embodiment, the frequency of the adoptive transfer of the NKT-like cells of the disclosure may be 2 times one month, each time transfusing $1\sim10\times10^{10}$ cells.

In an embodiment, the tumor may be selected from solid tumors and hematological neoplasms. Solid tumors include but not limited to, gastric cancer, esophageal cancer, small intestine cancer, colorectal cancer, colon cancer, rectal cancer, anal cancer, liver cancer, gallbladder cancer, breast cancer, ovarian cancer, cervical cancer, uterine cancer, pancreatic cancer, lung cancer, pharyngeal cancer, laryngeal cancer, nasopharyngeal cancer, thymoma, melanoma, testicular cancer, sarcoma, prostate cancer, metastatic cancer, renal cancer, melanoma, etc. Hematological neoplasms include but not limited to, myeloid malignancies, lymphatic malignancies, malignant histiocytosis and mast cell leukemia, wherein the myeloid malignancies include but not limited to myeloproliferative disorders (MPD), myelodysplastic syndrome (MDS), myelodysplastic/myeloproliferative disorders (MD/MPD) and acute myeloid leukemia (AML); the lymphatic malignancies include but not limited to T/NK cell tumor, B cell tumor and Hodgkin's disease.

In a preferred embodiment, the subject may be a mammal, preferably selected from cattle, horse, dog, goat, sheep, pig, camel, rat, mouse, monkey and human, and more preferably human. The subject may also be pet animals.

In the disclosure, the method of using the NKT-like cells of the disclosure to treat tumor (sometimes referred to herein as "the therapeutic method of the disclosure") is essentially a kind of immune cell therapy which may be performed in combination with other conventional methods of treating tumor (include but not limited to surgery, chemotherapy, radiotherapy, targeted therapy, traditional Chinese medicine, etc.). Here, any surgical procedure, chemotherapy regimen and chemotherapeutic, radiotherapy means and regimen, targeted therapy and targeted drug, traditional Chinese medicine regimen and traditional Chinese medicine, and the like that existed in the prior art before the filing date of the application and would be developed in the future may be used in the disclosure without any limitations. The specific combination of the described methods will be synthetically judged and determined by the clinician according to the specific conditions of the patient.

Preferably, the therapeutic method of the disclosure may be performed in combination with conventional tumor treatments. More preferably, the therapeutic method of the disclosure may be performed the therapeutic method of the disclosure may be performed after the tumor burden is reduced by conventional tumor treatment(s). In a typical regimen, the therapeutic method of the disclosure may be performed after the primary lesion(s) is (are) surgically resected and postoperative chemotherapy is accomplished. In another typical regimen, the therapeutic method of the disclosure may be performed after radiotherapy is accomplished. In a typical treatment, the therapeutic method of the disclosure may be performed after radiotherapy and chemotherapy are accomplished. Clinician may synthetically determine the combined therapy regimen for treating tumor and the timing of applying the therapeutic method of the disclosure according to the specific state of the patient, for example, tumor size, tumor stage, location, nature, pathological type and diagnosis, the patients' general condition, previous treatments and other factors.

The Safety Evaluation for the Treatment of Tumor with the NKT-Like Cells of the Disclosure The following table 2, table 3, and table 4 show the safety evaluation for the treatment of tumor with the NKT-like cells of the disclosure. No abnormal results were observed in recipient mice in in vivo tumorigenicity test, abnormal toxicity test and acute toxicity test.

Table 2 shows the results of in vivo tumorigenicity test of the CD8+NKT-like cells disclosed herein.

TABLE 2

In vivo tumorigenicity test of CD8+NKT-like cells

| Groups | Number of nude mice | Injection dose (cells) | Number of animals bearing tumor | The number of animals without tumor | The rate of tumor formation (%) |
|---|---|---|---|---|---|
| Experimental group | 10 | $4 \times 10^7$ CD8+NKT-like cells | 0 | 10 | 0 |
| Negative control group | 10 | $4 \times 10^7$ PBMC | 0 | 10 | 0 |
| Positive control group | 10 | $1 \times 10^6$ HELA | 10 | 0 | 100% |

Table 3 shows the results of abnormal toxicity test of the CD8+NKT-like cells disclosed herein.

TABLE 3

Abnormal toxicity test of CD8+NKT-like cells

| Groups | Number of animals | Injection dose (cells) | Weight | Hair color | Feces | Action | Appetite |
|---|---|---|---|---|---|---|---|
| Experimental group | 10 | $1 \times 10^6$ | Increase | Normal | Normal | Normal | Normal |
| Control group | 10 | PBS | Increase | Normal | Normal | Normal | Normal |

Table 4 shows the results of acute toxicity test of the CD8+NKT-like cells disclosed herein.

TABLE 4

Acute toxicity test of CD8+NKT-like cells

| Groups | Number of animals | Injection dose (cells) | Death | Hair color | Feces | Action | Appetite | Viscera |
|---|---|---|---|---|---|---|---|---|
| Intravenous injection experimental group | 10 | $4 \times 10^7$ | None | Normal | Normal | Normal | Normal | No Abnormality |
| Intravenous injection control group | 10 | PBS | None | Normal | Normal | Normal | Normal | No Abnormality |
| Intraperitoneal injection experimental group | 10 | $4 \times 10^7$ | None | Normal | Normal | Normal | Normal | No Abnormality |
| Intraperitoneal injection control group | 10 | PBS | None | Normal | Normal | Normal | Normal | No Abnormality |

Note:
The injection dose is 20 times the normal dose of cell reinfusion in human.

Therefore, it is safe to transfuse the CD8+NKT-like cells disclosed herein into the subject.

The preferred embodiments of the disclosure include:
1. An isolated NKT-like cell subpopulation, comprising NKT-like cells expressing CD8 molecule.
2. The NKT-like cell subpopulation according to Embodiment 1, characterized in that the NKT-like cell subpopulation comprises 50% or more, preferably 60% or more, more preferably 70% or more, most preferably 80% or more of the NKT-like cells expressing CD8 molecule.
3. The NKT-like cell subpopulation according to Embodiment 2, characterized in that the NKT-like cell subpopulation comprises 100% of the NKT-like cells expressing CD8 molecule.
4. The NKT-like cell subpopulation according to any one of Embodiments 1 to 3, characterized in that the NKT-like cells expressing CD8 molecule express CD3 and CD56, but not Vα24 TCR.
5. The NKT-like cell subpopulation according to any one of Embodiments 1 to 3, characterized in that the NKT-like cells expressing CD8 molecule express CD3 and CD161c, but not Vα14 TCR.
6. The NKT-like cell subpopulation according to Embodiment 4 or Embodiment 5, characterized in that TCRαβ is also expressed on the surface of the NKT-like cells expressing CD8 molecule.
7. The NKT-like cell subpopulation according to any one of Embodiments 1 to 6, characterized in that the NKT-like cell subpopulation is isolated from a mammal.
8. The NKT-like cell subpopulation according to Embodiment 7, characterized in that the mammal is a species selected from the group consisting of bovidae, equidae, felidae, canidae, leporidae, suidae, camelidae, rodent and primate, preferably being a cattle, a horse, a dog, a goat, a sheep, a cat, a rabbit, a pig, a camel, an alpaca, a rat, a mouse, a guinea pig, a non-human primate or a human, more preferably being a cattle, a horse, a dog, a goat, a sheep, a pig, a camel, a rat, a mouse, a monkey or a human.

9. The NKT-like cell subpopulation according to Embodiment 7, characterized in that the mammal is a pet animal, preferably being a pet dog, a pet cat, a pet rodent, or a pet rabbit.

10. Use of the NKT-like cell subpopulation according to any one of Embodiments 1 to 9 in the preparation of the medicament for the treatment of tumor.

11. A therapeutical composition comprising the NKT-like cell subpopulation according to any one of Embodiments 1 to 9 as a main active ingredient.

12. The therapeutical composition according to Embodiment 11, further comprising a pharmaceutical acceptable carrier, diluent, excipient, and/or additive.

13. Use of the therapeutical composition according to Embodiment 11 or Embodiment 12 in the preparation of the medicament for the treatment of tumor.

14. The use according to Embodiment 10 or Embodiment 13, characterized in that the tumor is a solid tumor or a hematological neoplasm.

15. The use according to Embodiment 14, characterized in that the solid tumor is selected from the group consisting of gastric cancer, esophageal cancer, small intestine cancer, colorectal cancer, colon cancer, rectal cancer, anal cancer, liver cancer, gallbladder cancer, breast cancer, ovarian cancer, cervical cancer, uterine cancer, pancreatic cancer, lung cancer, pharyngeal cancer, laryngeal cancer, nasopharyngeal cancer, thymoma, melanoma, testicular cancer, sarcoma, prostate cancer, metastatic cancer, renal cancer, and melanoma.

16. The use according to Embodiment 14, characterized in that the hematological neoplasm is selected from the group consisting of myeloid malignancy, lymphatic malignancy, malignant histiocytosis and mast cell leukemia.

17. The use according to Embodiment 14, characterized in that the myeloid malignancy is selected from the group consisting of myeloproliferative disorders (MPD), myelodysplastic syndrome (MDS), myelodysplastic/myeloproliferative disorders (MD/MPD) and acute myeloid leukemia (AML).

18. The use according to Embodiment 16, characterized in that the lymphatic malignancy is selected from the group consisting of T/NK cell tumor, B cell tumor and Hodgkin's disease.

19. The preparation method of the NKT-like cell subpopulation according to any one of Embodiments 1 to 9, comprising the following steps:
1) collecting peripheral blood from a subject, separating and removing red blood cells from the peripheral blood;
2) isolating mononuclear cells from the peripheral blood obtained in step 1) from which red blood cells have been removed, and sorting the NKT-like cell subpopulation according to any one of Embodiments 1 to 9 by using a cell sorting technique with the surface markers of the NKT-like cells expressing CD8 molecule according to any one of Embodiments 1 to 9;
3)/n vitro culturing the NKT-like cell subpopulation obtained in step 2), and adding to the culture cytokine(s) that can be able to stimulate the proliferation and activation of T cell, for a period of time enough to amplify the number of the NKT-like cells by at least 10~1000 times; and
4) harvesting the NKT-like cell subpopulation obtained in step 3).

20. The method according to Embodiment 19, characterized in that in step 3), the NKT-like cell subpopulation is cultured in vitro for 7 to 30 days, preferably 10 to 27 days, more preferably 14 to 21 days.

21. The method according to Embodiment 19, characterized in that in step 3), the NKT-like cell subpopulation is amplified to $1\times10^9 \sim 1\times10^{12}$ cells, preferably $1\sim10\times10^{10}$ cells.

22. The preparation method of the NKT-like cell subpopulation according to any one of Embodiments 1 to 9, comprising the following steps:
1) collecting peripheral blood from a subject, separating and removing red blood cells from the peripheral blood;
2) isolating mononuclear cells from the peripheral blood obtained in step 1) from which red blood cells have been removed, in vitro culturing the isolated mononuclear cells, and adding to the culture cytokine(s) that can be able to stimulate the proliferation and activation of T cell, for a period of time enough to amplify the number of the cells by at least 10~1000 times;
3) sorting the NKT-like cell subpopulation according to any one of Embodiments 1 to 9 by using a cell sorting technique with the surface markers of the NKT-like cells expressing CD8 molecule according to any one of Embodiments 1 to 9; and
4) harvesting the NKT-like cell subpopulation obtained in step 3).

23. The method according to Embodiment 22, characterized in that in step 2), the mononuclear cells are cultured in vitro for 7 to 30 days, preferably 10 to 27 days, more preferably 14 to 21 days.

24. The method according to Embodiment 22, characterized in that in step 2), the mononuclear cells are amplified to $1\times10^9 \sim 1\times10^{12}$ cells, preferably $1\sim10\times10^{10}$ cells.

25. The method according to any one of Embodiments 19-24, characterized in that the surface markers comprise CD3, CD56 and Vα24 TCR.

26. The method according to any one of Embodiments 19-24, characterized in that the surface markers comprise CD3, CD161c and Vα14 TCR.

27. The method according to Embodiment 25 or 26, characterized in that the surface markers further comprise TCRαβ.

28. The method according to any one of Embodiments 19-27, characterized in that the cytokine is one selected from the group consisting of GM-CSF, IL-2, IL-4, IL-5, IL-6, IL-7, IL-9, IL-12, IL-15, 4-1BBL or any combination thereof.

29. A method of treating a tumor in a subject in need thereof, comprising the following steps:
1) collecting peripheral blood from the subject;
2) isolating mononuclear cells from the peripheral blood of the subject, enriching the NKT-like cells according to any one of Embodiments 1 to 9 and amplifying the NKT-like cells in vitro; and
3) harvesting the amplified NKT-like cells obtained in step 2) and then adoptive transferring the amplified cells into the subject.

30. The method according to Embodiment 29, characterized in that the subject is a mammal 31. The method according to Embodiment 30, characterized in that the mammal is a species selected from the group consisting of bovidae, equidae, felidae, canidae, leporidae, suidae, camelidae, rodent and primate, preferably being a cattle, a horse, a dog, a goat, a sheep, a cat, a rabbit, a pig, a camel, an alpaca, a rat, a mouse, a guinea pig, a non-human primate or a human, more preferably being a cattle, a horse, a dog, a goat, a sheep, a pig, a camel, a rat, a mouse, a monkey or a human.

32. The method according to Embodiment 30, characterized in that the mammal is a pet animal, preferably being a pet dog, a pet cat, a pet rodent, or a pet rabbit.

33. The method according to any one of Embodiments 29-32, characterized in that the tumor is a solid tumor or a hematological neoplasm.

34. The method according to Embodiment 33, characterized in that the solid tumor is selected from the group consisting of gastric cancer, esophageal cancer, small intestine cancer, colorectal cancer, colon cancer, rectal cancer, anal cancer, liver cancer, gallbladder cancer, breast cancer, ovarian cancer, cervical cancer, uterine cancer, pancreatic cancer, lung cancer, pharyngeal cancer, laryngeal cancer, nasopharyngeal cancer, thymoma, melanoma, testicular cancer, sarcoma, prostate cancer, metastatic cancer, renal cancer, and melanoma.

35. The method according to Embodiment 33, characterized in that the hematological neoplasm is selected from the group consisting of myeloid malignancy, lymphatic malignancy, malignant histiocytosis and mast cell leukemia.

36. The method according to Embodiment 35, characterized in that the myeloid malignancy is selected from the group consisting of myeloproliferative disorders (MPD), myelodysplastic syndrome (MDS), myelodysplastic/myeloproliferative disorders (MD/MPD) and acute myeloid leukemia (AML).

37. The method according to Embodiment 35, characterized in that the lymphatic malignancy is selected from the group consisting of T/NK cell tumor, B cell tumor and Hodgkin's disease.

38. The method according to any one of Embodiments 29-37, characterized in that in step 3), the NKT-like cells are intravenously infused.

39. The method according to any one of Embodiments 29-37, characterized in that in step 3), the NKT-like cells are intratumorally injected.

40. The method according to any one of Embodiments 29-37, characterized in that in step 3), the NKT-like cells are intraperitoneally perfused.

41. The method according to any one of Embodiments 29-40, characterized in that in step 2), the NKT-like cells are amplified to $1 \times 10^9 \sim 1 \times 10^{12}$ cells, preferably $1 \sim 10 \times 10^{10}$ cells.

42. A method of treating a tumor in a subject in need thereof, comprising the following steps:
   1) collecting peripheral blood from the subject;
   2) isolating mononuclear cells from the peripheral blood of the subject and in vitro amplifying the isolated mononuclear cells,
   3) enriching the NKT-like cells according to any one of Embodiments 1 to 9 from the amplified cells obtained in step 2); and
   4) harvesting the enriched NKT-like cells obtained in step 3) and then adoptive transferring the enriched cells into the subject.

43. The method according to Embodiment 42, characterized in that the subject is a mammal.

44. The method according to Embodiment 43, characterized in that the mammal is a species selected from the group consisting of bovidae, equidae, felidae, canidae, lepori-dae, suidae, camelidae, rodent and primate, preferably being a cattle, a horse, a dog, a goat, a sheep, a cat, a rabbit, a pig, a camel, an alpaca, a rat, a mouse, a guinea pig, a non-human primate or a human, more preferably being a cattle, a horse, a dog, a goat, a sheep, a pig, a camel, a rat, a mouse, a monkey or a human.

45. The method according to Embodiment 43, characterized in that the mammal is a pet animal, preferably being a pet dog, a pet cat, a pet rodent, or a pet rabbit.

46. The method according to any one of Embodiments 42-45, characterized in that the tumor is a solid tumor or a hematological neoplasm.

47. The method according to Embodiment 46, characterized in that the solid tumor is selected from the group consisting of gastric cancer, esophageal cancer, small intestine cancer, colorectal cancer, colon cancer, rectal cancer, anal cancer, liver cancer, gallbladder cancer, breast cancer, ovarian cancer, cervical cancer, uterine cancer, pancreatic cancer, lung cancer, pharyngeal cancer, laryngeal cancer, nasopharyngeal cancer, thymoma, melanoma, testicular cancer, sarcoma, prostate cancer, metastatic cancer, renal cancer, and melanoma.

48. The method according to Embodiment 46, characterized in that the hematological neoplasm is selected from the group consisting of myeloid malignancy, lymphatic malignancy, malignant histiocytosis and mast cell leukemia.

49. The method according to Embodiment 48, characterized in that the myeloid malignancy is selected from the group consisting of myeloproliferative disorders (MPD), myelodysplastic syndrome (MDS), myelodysplastic/myeloproliferative disorders (MD/MPD) and acute myeloid leukemia (AML).

50. The method according to Embodiment 48, characterized in that the lymphatic malignancy is selected from the group consisting of T/NK cell tumor, B cell tumor and Hodgkin's disease.

51. The method according to any one of Embodiments 42-47, characterized in that in step 4), the NKT-like cells are intravenously infused.

52. The method according to any one of Embodiments 42-47, characterized in that in step 4), the NKT-like cells are intratumorally injected.

53. The method according to any one of Embodiments 42-47, characterized in that in step 4), the NKT-like cells are intraperitoneally perfused.

54. The method according to any one of Embodiments 42-53, characterized in that in step 2), the mononuclear cells are amplified to $1 \times 10^9 \sim 1 \times 10^{12}$ cells, preferably $1 \sim 10 \times 10^{10}$ cells.

The disclosure is further described by the following examples, but the examples are only used for the purpose of illustrating the invention rather than limiting the scope of the invention. Other embodiments will be apparent to a person skilled in the art when reading the specification with reference to the common knowledge.

The following experimental methods described in the examples are the conventional methods unless specifically stated. The experimental materials used in the following examples are available from the commercial companies unless specifically stated.

EXAMPLES

Example 1: The Detection of the Phenotype of Mouse CD8$^+$NKT-Like Cells (1) Mouse spleen cells were isolated, and mononuclear cells were separated from the spleen cells by density gradient centrifugation with Ficoll medium having a density of 1.083.

(2) PanNK positive cells were sorted out from the mouse spleen cells according to the requirement of panNK Positive Sorting Kit available from Stemcell Inc. The experimental steps were specifically listed as follows:
  i) the spleen mononuclear cells were resuspended in PBS buffer to $10^8$/mL;
  ii) CD49b-PE (CD49b is a marker of panNK positive cells) was added in an amount of 50 μL/mL cell suspension, and incubated away from light at room temperature for 15 minutes;
  iii) a cocktail liquid was added in an amount of 100 μL/mL cell suspension, and incubated away from light at room temperature for 15 minutes;
  iv) magnetic beads were added in an amount of 50 μL/mL cell suspension, and incubated away from light at room temperature for 10 minutes;
  v) PBS was added to the cell suspension to reach a total volume of 2.5 mL, and then the resulting cell suspension was transferred to a 5 mL BD Falcon flow cytometry injection tube which was subsequently placed in a Stemcell positive sorting magnet and let stand for 5 minutes;
  vi) the magnet was picked up and the negative cells were discarded;
  vii) the cell pellet was resuspended in 2.5 mL PBS, and the resulting cell suspension was placed in a Stemcell positive sorting magnet and let stand for 5 minutes;
  viii) the magnet was picked up and the negative cells were discarded; and
  ix) the BD Falcon flow cytometry injection tube was taken from the magnet, and the positive cells were resuspended in 500 μL PBS.
(3) The positive cells were resuspended in 200 μL PBS, labeled with 10 μL APC labeled α-GalCer-loaded CD1d tetramer (Proimmune Inc.), and then incubated at 4° C. for 30 minutes.
(4) The cells were washed one time with 1 mL PBS. The cells were resuspended in 500 μL PBS, and labeled after subpackaged in tubes at 50 μL/tube (note: all fluorescent antibodies were purchased from BioLegend Inc., unless specifically stated):
  Tube 1 was used to label TCRβ-FITC, CD8-PerCP, CD3-APC-Cy7, NK1.1-PE-Cy7.
  Tube 2 was used to label TCRβ-FITC, CD8-APC-Cy7, NKG2D-PE-Cy7, CD44-PerCP.
  Tube 3 was used to label TCRβ-APC-Cy7, CD8-PerCP, KLRG1-PE-Cy7, Ly49G2-FITC (eBioscience Inc.).
  Tube 4 was used to label TCRβ-APC-Cy7, CD8-PerCP, CD27-PE-Cy7, NKG2A/C/E-FITC.
  Tube 5 was used to label TCRβ-APC-Cy7, CD8-PE-Cy7, CD62L-FITC, CD122-PerCP.
  Tubes 6-10 were used to label corresponding isotype control antibodies of the above-mentioned antibodies (available from BioLegend Inc.).
(5) Each sample tube was incubated at 4° C. for 30 minutes.
(6) Each sample tube was added 1 mL PBS, centrifuged at 1500 rpm for 10 minutes, and the supernatant was discarded.
(7) Step (6) was repeated, and the cell pellet was resuspended in 300 μL PBS.
(8) The cell suspension was loaded on a BD FACSAria II flow cytometry. The detection of CD8$^+$DX5$^+$TCRβ$^+$ CD1d Tetramer$^-$ cells (mouse CD8$^+$NKT-like cells) was performed.
The results showed that the mouse CD8$^+$ NKT-like cells expressed T cell lineage marker CD3 and TCRβ as well as NK cell lineage marker NK1.1(CD161c), but did not express iNKT lineage marker CD1d. In addition, it can also be seen from FIG. 1 that the CD8$^+$ NKT-like cells disclosed herein expressed T cell activation markers (CD44. CD62L and CD122) as well as NK cell receptors (NKG2A/C/E, KLRG1, NKG2D, Ly49G$_2$ and CD27).

Example 2: Phenotypic Differences Between Mouse CD8$^+$NKT-Like Cells Disclosed Herein and Mouse NK Cells, Mouse iNKT Cells and Mouse CTL Cells (1) Mouse spleen cells were isolated, and mononuclear cells were separated from the spleen cells by density gradient centrifugation with Ficoll medium having a density of 1.083.
(2) PanNK positive cells were sorted out from the mouse spleen cells according to the requirement of panNK Positive Sorting Kit available from Stemcell Inc. The experimental steps were specifically listed as follows:
  i) the spleen mononuclear cells were resuspended in PBS buffer to $10^8$/mL;
  ii) CD49b-PE (CD49b is a marker of panNK positive cells) was added in an amount of 50 μL/mL cell suspension, and incubated away from light at room temperature for 15 minutes;
  iii) a cocktail liquid was added in an amount of 100 μL/mL cell suspension, and incubated away from light at room temperature for 15 minutes;
  iv) magnetic beads were added in an amount of 50 μL/mL cell suspension, and incubated away from light at room temperature for 10 minutes;
  v) PBS was added to the cell suspension to reach a total volume of 2.5 mL, and then the resulting cell suspension was transferred to a 5 mL BD Falcon flow cytometry injection tube which was subsequently placed in a Stemcell positive sorting magnet and let stand for 5 minutes;
  vi) the magnet was picked up and the negative cells were poured into a new centrifuge tube;
  vii) the cell pellet was resuspended in 2.5 mL PBS, and the resulting cell suspension was placed in a Stemcell positive sorting magnet and let stand for 5 minutes;
  viii) the magnet was picked up and the negative cells were discarded; and
  ix) the BD Falcon flow cytometry injection tube was taken from the magnet, and the positive cells were resuspended in 500 μL PBS.
(3) The positive cells were resuspended in 200 μL PBS, labeled with 10 μL APC labeled α-GalCer-loaded CD1d tetramer (Proimmune Inc.), and then incubated at 4° C. for 30 minutes.
(4) The cells were washed one time with 1 mL PBS. The cells were resuspended in 500 μL PBS, and labeled after subpackaged in tubes at 50 μL/tube (all purchased from BioLegend Inc.):
  Tube 1 was used to label TCRβ-FITC, CD8-PerCP, CD3-APC-Cy7, NK1.1-PE-Cy7.
  Tube 2 was used to label TCRβ-FITC, CD8-APC-Cy7, NKG2D-PE-Cy7.
  Tube 3 was used to label TCRβ-APC-Cy7, CD8-PerCP, KLRG1-PE-Cy7, Ly6G-FITC.
  Tube 4 was used to label TCRβ-APC-Cy7, CD8-PerCP, CD27-PE-Cy7, NKG2A/C/E-FITC.
  Tubes 5-8 were used to label corresponding isotype control antibodies of the above-mentioned antibodies (available from BioLegend Inc.).

(5) Each sample tube was incubated at 4° C. for 30 minutes.
(6) Each sample tube was added 1 mL PBS, centrifuged at 1500 rpm for 10 minutes, and the supernatant was discarded.
(7) Step (6) was repeated, and the cell pellet was resuspended in 300 μL PBS.
(8) The cell suspension was loaded on a BD FACSAria II flow cytometry. CD8$^+$DX5$^+$TCRβ$^+$CD1d Tetramer$^-$ cells (mouse CD8$^+$NKT-like cells), CD8$^-$DX5$^+$TCRβ$^+$CD1d Tetramer cells (mouse iNKT cells), CD8$^+$DX5$^-$TCRβ$^+$CD1d Tetramer$^-$ cells (mouse CD8$^+$ T cells), and DX5$^+$TCRβ$^-$ cells (mouse NK cells) were gated to analyze these phenotypes.

The results showed that there are phenotypic differences between the CD8$^+$NKT-like cells disclosed herein and NK cells, iNKT cells and CTL cells in mice. It can be seen from FIG. 2 that: (1) compared with NK cells, the CD8$^+$NKT-like cells expressed not only NK cell markers [NK1.1 (CD161c), NKG2A/C/E, CD27, KLRG1 and Ly6G], but also TCRβ and CD3 which were not expressed on the NK cells; (2) compared with CTL cells, the CD8$^+$NKT-like cells expressed T cell lineage markers (TCRβ and CD3), but did not express NK cell receptors; (3) compared with iNKT cells, the CD8$^+$NKT-like cells cannot bind to the CD1d tetramer loaded with lipid antigens.

Example 3: The Transmission Electron Micrographs and the Laser Confocal Micrographs of CD8$^+$NKT-Like Cells, NK Cells and CD8$^+$T Cells (1) Mouse spleen cells were isolated, and mononuclear cells were separated from the spleen cells by density gradient centrifugation with Ficoll medium having a density of 1.083.
(2) PanNK positive cells were sorted out from the mouse spleen cells according to the requirement of panNK Positive Sorting Kit available from Stemcell Inc. The experimental steps were specifically listed as follows:
i) the spleen mononuclear cells were resuspended in PBS buffer solution to 10$^8$/mL;
ii) CD49b-PE (CD49b is a marker of panNK positive cells) was added in an amount of 50 μL/mL cell suspension, and incubated away from light at room temperature for 15 minutes;
iii) a cocktail liquid was added in an amount of 100 μL/mL cell suspension, and incubated away from light at room temperature for 15 minutes;
iv) magnetic beads were added in an amount of 50 μL/mL cell suspension, 20 μL/mL TCRβ-FITC and CD8-APC-Cy7 were further added, and the resulting cell suspension was incubated away from light at room temperature for 10 minutes;
v) PBS was added to the cell suspension to reach a total volume of 2.5 mL, and then the resulting cell suspension was transferred to a 5 mL BD Falcon flow cytometry injection tube which was subsequently placed in a Stemcell positive sorting magnet and let stand for 5 minutes;
vi) the magnet was picked up and the negative cells were poured into a new centrifuge tube;
vii) the cell pellet was resuspended in 2.5 mL PBS, and the resulting cell suspension was placed into a Stemcell positive sorting magnet and let stand for 5 minutes;
viii) the magnet was picked up and the negative cells were discarded; and
ix) the BD Falcon flow cytometry injection tube was taken from the magnet.

(3) The positive cells were resuspended in 200 μL PBS, labeled with 10 μL APC labeled α-GalCer-loaded CD1d tetramer (Proimmune Inc.), and then incubated at 4° C. for 30 minutes.
(4) The cells were washed one time with 1 mL PBS. The positive cells were resuspended in 500 μL PBS, and then loaded on a BD FACSAria II flow cytometry to sort CD8$^+$DX5$^+$TCRβ$^+$ cells (mouse CD8$^+$NKT-like cells) and DX5$^+$TCRβ$^-$ cells (mouse NK cells) by gating; the negative cells were loaded to sort CD8$^+$DX5$^-$TCRβ$^+$ cells (mouse CD8$^+$ T cells).
(5) The CD8$^+$NKT-like cells, CD8$^+$ T cells and NK cells were plated at a density of 2×10$^6$/mL into 96-well plates, respectively, and 1640 complete culture medium containing 50 ng/mL IL-2, 10 ng/mL IL-4, 10 ng/mL IL-5, 100 ng/mL IL-6, 80 ng/mL IL-7, 1 ng/mL IL-9, 100 ng/mL IL-12, 20 ng/mL IL-15, 10 ng/mL GM-CSF and 20 ng/mL 4-1BBL was added into each well. The cells were harvested after cultured in vitro for 5 days, and then sampled for TEM (Transmission Electron Microscope) scanning and LSCM (Laser Scanning Confocal Microscope) scanning.
(6) The morphologies of CD8$^+$NKT-like cells, CD8$^+$ T cells and NK cells were observed under a LSCM. The experimental protocol included the following steps:
i) all of the densities of three kinds of cells was adjusted in PBS buffer to 1×10$^6$/ml;
ii) CD90.2-FITC antibody was added at a ratio of 1:100 by volume, and LysoTracker dye was added to a final concentration of 1 μmol/L. The resulting mixture was incubated at 4° C. for 30 minutes; and
iii) the cells was sufficiently washed 2 times with PBS buffer and added Hoechst 33342 dye at a final concentration of 10 μg/ml. The cells were observed after incubated at room temperature for 10 minutes.

The transmission electron micrographs of FIG. 3A showed that the CD8$^+$NKT-like cells contained a large amount of granular substances, while the NK cells and the CD8$^+$ T cells contained less similar granular substances. The laser confocal micrographs of FIG. 3B showed that the volume of CD8$^+$NKT-like cells disclosed herein was larger and its diameter was more than about 15 μm, while the diameters of NK cells and CD8$^+$ T cells were less than 10 μm, being about 7 μm. At the same time, the granular substance in the CD8$^+$NKT-like cells was positive for lysosomal dye staining, suggesting that these granular substances may contain granzyme that elicits a cytotoxic effect, while the NK cells and the CD8$^+$ T cells contained less granules that are positive for lysosomal dye staining. In addition, the staining of the nucleus and cell membrane showed that the nuclear-cytoplasmic ratio of the CD8$^+$NKT-like cells was smaller than that of other two kinds of cells.

Example 4: Comparison of Cytokine Secretory Abilities of Mouse CD8$^+$NKT-Like Cells, Mouse CD8$^+$T Cells and Mouse CD4$^+$T Cells 1. Isolation of CD8$^+$NKT-Like Cells and CD8$^+$T Cells from OT-I Mice
(1) OT-I mouse spleen cells were isolated, and mononuclear cells were separated from the spleen cells by density gradient centrifugation with Ficoll medium having a density of 1.083.
(2) PanNK positive cells were sorted out from the OT-I mouse spleen cells according to the requirement of panNK Positive Sorting Kit available from Stemcell Inc. The experimental steps were specifically listed as follows:

i) the spleen mononuclear cells were resuspended in PBS buffer solution to $10^8$/mL;
ii) CD49b-PE (CD49b is a marker of panNK positive cells) was added in an amount of 50 μL/mL cell suspension, and incubated away from light at room temperature for 15 minutes;
iii) a cocktail liquid was added in an amount of 100 μL/mL cell suspension, and incubated away from light at room temperature for 15 minutes;
iv) magnetic beads were added in an amount of 50 μL/mL cell suspension, 20 μL/mL TCRβ-FITC and CD8-APC-Cy7 were further added, and the cell suspension was incubated away from light at room temperature for 10 minutes;
v) PBS was added to the cell suspension to reach a total volume of 2.5 mL, and then the cell suspension was transferred to a 5 mL BD Falcon flow cytometry injection tube which was subsequently placed in a Stemcell positive sorting magnet and let stand for 5 minutes;
vi) the magnet was picked up and the negative cells were poured into a new centrifuge tube;
vii) the cell pellet was resuspended in 2.5 mL PBS, and the resulting cell suspension was placed in a Stemcell positive sorting magnet and let stand for 5 minutes;
viii) the magnet was picked up and the negative cells were discarded; and
ix) the BD Falcon flow cytometry injection tube was taken from the magnet, and positive cells were resuspended in 500 μL PBS.
(3) The positive cells were resuspended in 200 μL PBS, labeled with 10 μL APC labeled α-GalCer-loaded CD1d tetramer (Proimmune Inc.), and then incubated at 4° C. for 30 minutes.
(4) The cells were washed with 1 mL PBS one time. The positive cells were resuspended in 500 μL PBS, and then loaded on a BD FACS Aria II flow cytometry to sort $CD8^+DX5^+TCRβ^+$ cells (mouse $CD8^+$NKT-like cells) by gating; the negative cells were loaded to sort $CD8^lDX5^-TCRβ^l$ cells (mouse $CD8^+$ T cells).
2. Isolation of $CD4^+$T Cells from OT-II Mice
(1) OT-II mouse spleen cells were isolated, and mononuclear cells were separated from the spleen cells by density gradient centrifugation with Ficoll medium having a density of 1.083.
(2) $CD4^+$ T cells were sorted out from the OT-II mouse spleen cells according 1.0 to the requirement of CD4 Positive Sorting Kit available from Miltenyi Inc. The experimental steps were specifically listed as follows:
i) the spleen mononuclear cells were resuspended in PBS buffer solution to $10^8$/mL;
ii) magnet beads coupled with anti-mouse CD4 antibody were added in an amount of 100 μL/mL cell suspension, and incubated away from light at 4° C. for 15 minutes;
iii) the labeled cells were resuspended in 2 mL PBS, and loaded on the Miltenyi magnetic separation column;
iv) 2 mL PBS was further added after the liquid completely passed through the column, and repeated one time; and
v) the magnet and the sorting column were detached, and the positive cells with a purity of more than 90% were eluted.
3. The Detection of Antigen Specific Activation and Intracellular Cytokines of Lymphocyte Populations
(1) The cells were resuspended in 1640 culture medium containing 10% fetal bovine serum, and seeded into 96-well round bottom culture plates at a density of $8 \times 10^4$ cells/well. $1 \times 10^4$ dendritic cells loaded with antigens per well (the final concentration of $OVA_{257-264}$ peptide fragment added was 1 μg/mL for OT-I mice derived $CD8^+$ NKT-like cells and $CD8^+$ T cells; the final concentration of $OVA_{323-339}$ peptide fragment added was 1 μg/mL for OT-II mice derived $CD4^+$ T cells) were added to each well for antigen challenge. The total volume of the culture medium in each well was 100 μL.
(2) The culture supernatant was collected at 24 hr and 48 hr of culture, respectively. The concentration of cytokines was detected by Th cytokine detection kit from eBioscience Inc. (BMS822FF mouse Th1/Th2/Th17/Th22 13plex). The protocols were performed in accordance with the instruction and the description of the specific steps was omitted for the sake of simplicity.

It can be seen from FIG. 4 that the level of IFN-γ secreted by the $CD8^+$NKT-like cells was significantly higher than those by $CD8^+$ T cells and $CD4^+$ T cells at 24 hr and 48 hr after challenged by specific antigens; the level of IL-2 secreted by $CD8^+$NKT-like cells was lower than $CD8^+$ T cells, and was comparable to $CD4^+$ T cells. With regard to cell factor expression profile, both the expressions of IFN-γ and IL-2 were higher in $CD8^+$ T cells relative to $CD4^+$ T cells, while only the expression of IFN-γ was higher in the $CD8^+$NKT-like cells of the disclosure relative to $CD4^+$ T cells.

Example 5: A Flow Chart of an Example of the Method of In Vitro Amplifying Human $CD8^+$NKT-Like Cells (1) Human venous blood was drawn into a vacuum tube containing anticoagulant heparin, and mononuclear cells (PBMC) were separated from the blood by density gradient centrifugation with Ficoll lymphocyte separation medium having a density of 1.077(Sigma).
(2) PBMCs were resuspended in PBS buffer to a density of $2 \times 10^6$/mL. PerCP labeled anti-human CD3 antibody, PE labeled anti-human CD56 antibody, APC labeled anti-human CD8 antibody, PE-Cy7 labeled anti-human CD4 antibody, FITC labeled anti-human iNKT Vα24TCR antibody were added at 1:100, and then incubated at 4° C. for 30 minutes.
(3) The PBMCs were resuspended in 20 mL PBS and centrifuged at 1500 rpm for 10 minutes.
(4) Step (3) was repeated again.
(5) $CD3^+CD56^+Vα24TCR^-CD8^+CD4^-$ cell subpopulation was sorted out according to the gating strategy shown in the step 2 of FIG. 5.
(6) Cells were cultured at a density of $2 \times 10^6$/mL. The culture system was a serum-free Takara GT-T551(Takara Inc.) containing 50 ng/mL IL-2 (purchased from Peprotech Inc., hereinafter the same), 10 ng/mL IL-4, 10 ng/mL IL-5, 100 ng/mL IL-6, 80 ng/mL IL-7, 1 ng/mL IL-9, 100 ng/mL IL-12, 20 ng/mL IL-15, 10 ng/mL GM-CSF, and 20 ng/mL 4-1BBL.
(7) After 21 days of culture, cultured cells were collected for further use.

Example 6: The Ability of In Vitro Amplification of $CD8^+$NKT-Like Cells

1. The Ability of In Vitro Amplification of Mice $CD8^+$NKT-Like Cells:
(1) OT-I mice $CD8^+$NKT-like cells were sorted out according to the method of isolating OT-I mice $CD8^+$NKT-like cells as described in Example 4.
(2) OT-I mice $CD8^+$NKT-like cells were cultured at a density of $2 \times 10^6$/mL in 1640 medium (Gibco Inc.) containing 50 ng/mL IL-2 (purchased from Peprotech Inc., hereinafter the same), 10 ng/mL IL-4, 10 ng/mL IL-5, 100 ng/mL IL-6, 80 ng/mL IL-7, 1 ng/mL IL-9, 100 ng/mL IL-12, 20 ng/mL IL-15, 10 ng/mL GM-CSF, 20 ng/mL 4-1BBL and 10% fetal calf serum (Gibco Inc.); the dendritic cells loaded with 1 μg/mL $OVA_{257-264}$ antigen (synthesized by Chinese Peptide Company) were added at $1×10^4$ cells/well to the culture system.

(3) Cells were collected every 7 days after cultured. The cell number was counted by a hemocytometer and a cell growth curve was created.

2. The Ability of In Vitro Amplification of Human CD8+NKT-Like Cells:

(1) Human CD8+NKT-like cells were isolated according to the method of isolating human CD8+NKT-like cells as described in Example 5.

(2) Human CD8+NKT-like cells were cultured at a density of $2×10^6$/mL. The culture system was a serum-free Takara GT-T551(Takara Inc.) containing 50 ng/mL IL-2 (purchased from Peprotech Inc., hereinafter the same), 10 ng/mL IL-4, 10 ng/mL IL-5, 100 ng/mL IL-6, 80 ng/mL IL-7, 1 ng/mL IL-9, 100 ng/mL IL-12, 20 ng/mL IL-15, 10 ng/mL GM-CSF, and 20 ng/mL 4-1BBL.

(3) Cells were collected every 7 days after cultured. The cell number was counted by a hemocytometer and a cell growth curve was created.

Example 7: The Effects of Adoptive Transferring CD8+NKT-Like Cells and PBS on the Lung Metastases of Melanoma in Mice that had been Inoculated with B16 Melanoma Cells Via Tail Vein (1) Mouse CD8+NKT-like cells were isolated and in vitro amplified according to the methods described in Example 6.

(2) C57BL/6 female mice were seeded with $2×10^5$ B16-F10 melanoma cells via tail vein.

(3) 24 hours after seeding with tumor cells, the mice were intraperitoneally injected with the specified doses of CD8+NKT-like cells or PBS.

(4) The mice were sacrificed 14 days after seeded with tumor cells, lungs were separated, and the macroscopic melanoma metastases in each group were counted, taken photos and recorded.

Example 8: In Vitro Antigen-Specific Killing Effects of the Mouse CD8+NKT-Like Cells Having Different Antigen Specificities on EL4-OVA8 Tumor Cells (1) CD8+NKT-like cells from OT-I specific TCR transgenic mice (abbreviated as $NKT_{OVA}$) and SV specific TCR transgenic mice (abbreviated as $NKT_{SV}$) were in vitro amplified respectively according to the methods described in Example 4.

(2) EL4-OVA8 tumor cells were cultured in 1640 medium containing 10% fetal bovine serum.

(3) EL4-OVA8 cells were collected and resuspended in PBS at $1×10^6$/mL. A living cell fluorescent dye CMFDA (Life Technologies Corp.) was added at a final concentration of 1 μM, and incubated at 4° C. for 10 minutes.

(4) Tumor cells were washed with PBS buffer containing 10% fetal bovine serum. The tumor cells were seeded at $1×10^4$ cells/well into 96-well plates after recounted.

(5) The two kinds of CD8+NKT-like cells were collected, and were added at a ratio of effector to target of 20:1 into the wells which were seeded with target cells in advance. Each experiment was run in tuplicate.

(6) After the effector cells and the target cells were co-cultured for 24 hours, the remaining cells in each group were collected and labeled with 7-AAD. After incubated at 4° C. for 10 minutes, the ratio of 7-AAD positive cells in the fluorescent dye labeled target cells, namely, the killing rate of effector cells to target cells, was detected by a flow cytometry.

Example 9: The Effect of Adoptive Transferring CD8+NKT-Like Cells Having Different Antigen Specificities on the Curve of In Vivo Tumor Size and Survival Time in Mice Inoculated with EL4-OVA8 Tumor Cells (1) CD8+NKT-like cells from OT-I specific TCR transgenic mice (abbreviated as $NKT_{OVA}$) and SV specific TCR transgenic mice (abbreviated as $NKT_{SV}$) were in vitro amplified respectively according to the methods described in Example 4.

(2) EL4-OVA8 tumor cells were cultured in 1640 medium containing 10% fetal bovine serum.

(3) C57BL/6 female mice were subcutaneously seeded with $5×10^6$EL4-OVA8 tumor cells.

(4) 24 hours after seeding with tumor cells, different doses of $NKT_{OVA}$ and $NKT_{SV}$ cells ($5×10^5$ and $2.5×10^6$, respectively) or PBS were intraperitoneally injected into the mice.

(5) Subcutaneous tumor size was measured at different time points after seeding with tumor cells (represented in length (mm)×width (mm), see FIG. 9A, 9B).

Example 10: The Comparison of the Non-Antigen-Specific Killing Effects of the Mouse CD8+NKT-Like Cells and Mouse NK Cells on Yac-1 Tumor Cells (1) CD8+NKT-like cells (abbreviated as NKT) and NK cells (abbreviated as NK) were in vitro isolated from C57BL/6 mice, and activated according to the methods described in Example 3.

(2) Yac-1 tumor cells were cultured in 1640 medium containing 10% fetal bovine serum.

(3) Yac-1 cells were collected and resuspended in PBS at $1×10^6$/mL. A living cell fluorescent dye CMFDA (Life Technologies Corp.) was added at a final concentration of 1 μM, and incubated at 4° C. for 10 minutes.

(4) Tumor cells were washed with PBS buffer containing 10% fetal bovine serum. The tumor cells were seeded at $1×10^4$ cells/well into 96-well plates after recounted.

(5) The CD8+NKT-like cells and NK cells were collected, and were added at ratios of effector to target of 1:1, 5:1 and 20:1 into the wells which were seeded with target cells in advance, respectively. Each experiment was run in tuplicate.

(6) After the effector cells and the target cells were co-cultured for 24 hours, the remaining cells in each group were collected and labeled with 7-AAD. After incubated at 4° C. for 10 minutes, the ratio of 7-AAD positive cells in the fluorescent dye labeled target cells, namely, the killing rate of effector cells to target cells, was detected by a flow cytometry.

Example 11: The Comparison of the Killing Effects of the OVA Antigen Specific CD8+NKT-Like Cells and OVA Antigen Specific CD8+ T Cells on EL4-OVA8 Tumor Cells (1) CD8+NKT-like cells (abbreviated as $NKT_{OVA}$) and CD8+ T cells (abbreviated as $CTL_{OVA}$) were in vitro isolated from OT-I specific TCR transgenic mice, and activated according to the methods described in Example 4.

(2) EL4-OVA8 tumor cells were cultured in 1640 medium containing 10% fetal bovine serum.

(3) EL4-OVA8 cells were collected and resuspended in PBS at $1\times10^6$/mL. A living cell fluorescent dye CMFDA (Life Technologies Corp.) was added at a final concentration of 1 μM, and incubated at 4° C. for 10 minutes.

(4) Tumor cells were washed with PBS buffer containing 10% fetal bovine serum. The tumor cells were seeded at $1\times10^4$ cells/well into 96-well plates after recounted.

(5) The CD8+NKT-like cells and CD8+T cells were collected, and were added at a ratio of effector to target of 20:1 into the wells which were seeded with target cells in advance. Each experiment was run in tuplicate.

(6) After the effector cells and the target cells were co-cultured for 24 hours, the remaining cells in each group were collected and labeled with 7-AAD. After incubated at 4° C. for 10 minutes, the ratio of 7-AAD positive cells in the fluorescent dye labeled target cells, namely, the killing rate of effector cells to target cells, was detected by a flow cytometry.

Example 12: The Comparison of Expression Levels of Various Granzymes, Perforin and Lamp-1 on Mouse CD8+NKT-Like Cells, Mouse NK Cells and Mouse CD8 T Cells (1) CD8+NKT-like cells, NK cells and CD8 T cells were in vitro isolated from OT-1 specific TCR transgenic mice, and activated according to the methods described in Example 4.

(2) $1\times10^7$ of respective cells were collected, the supernatant was discarded after centrifugation, and then the cell pellets were resuspended in 1 ml Trizol and dispersed homogeneously with a pipette.

(3) The samples were sent to a gene company to perform expression profile analysis by using Affymetrix gene expression chip.

(4) R language was utilized to extract the expression profile of the genes that are associated with various cell granule release pathways, and the thermal maps were made for comparison.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCE

[1] Watzl, C. and Long, E. O., Exposing tumor cells to killer cell attack. Nat Med 2000.6: 867-868.

[2] Budd, R. C., Miescher, G. C., Howe, R. C., Lees, R. K., Bron, C. and MacDonald, H. R., Developmentally regulated expression of T cell receptor beta chain variable domains in immature thymocytes. J Exp Med 1987. 166: 577-582.

[3] Fowlkes, B. J., Kruisbeek, A. M., Ton-That, H., Weston, M. A., Coligan, J. E., Schwartz, R. H. and Pardoll, D. M., A novel population of T-cell receptor alpha beta-bearing thymocytes which predominantly expresses a single V beta gene family. Nature 1987. 329: 251-254.

[4] Ceredig, R., Lynch, F. and Newman, P., Phenotypic properties, interleukin 2 production, and developmental origin of a "mature" subpopulation of Lyt-2-L3T4-mouse thymocytes. Proc Natl Acad Sci USA 1987. 84: 8578-8582.

[5] Sykes, M., Unusual T cell populations in adult murine bone marrow. Prevalence of CD3+CD4−CD8− and alpha beta TCR+NK1.1+ cells. J Immunol 1990. 145: 3209-3215.

[6] Makino, Y., Kanno, R., Ito, T., Higashino, K. and Taniguchi, M., Predominant expression of invariant V alpha 14+ TCR alpha chain in NK1.1+ T cell populations. Int Immunol 1995. 7: 1157-1161.

[7] Godfrey, D. I., MacDonald, H. R., Kronenberg, M., Smyth, M. J. and Van Kaer, L., NKT cells: what's in a name? Nat Rev Immunol 2004. 4: 231-237.

[8] Maeda, M., Shadeo, A., MacFadyen, A. M. and Takei, F., CD1d-independent NKT cells in beta 2-microglobulin-deficient mice have hybrid phenotype and function of NK and T cells. J Immunol 2004. 172: 6115-6122.

What is claimed is:

1. A preparation method of isolated mammal NKT-like cells, comprising the following steps:
    1) collecting peripheral blood from a mammal subject, separating and removing red blood cells from the peripheral blood;
    2) isolating mononuclear cells from the peripheral blood obtained in step 1) from which red blood cells have been removed, and sorting the NKT-like cells by using a cell sorting technique with NKT-like cell surface markers;
    3) in vitro culturing the NKT-like cells obtained in step 2), and adding cytokine(s) that stimulate the proliferation and activation of T cell, for a period of time enough to amplify the number of the NKT-like cells by at least 10~1000 times; and
    4) harvesting the NKT-like cells obtained in step 3),
    wherein the NKT-like cell surface markers comprise CD8, CD3, TCRαβ, CD161c, CD44, CD62L, CD122, NKG2A/C/E, KLRG1, NKG2D, Ly49G2 and CD27, or comprise CD8, CD3, TCRαβ, CD56, CD44, CD62L, CD122, NKG2A/C/E, KLRG1, NKG2D, Ly49G2 and CD27.

2. The method according to claim 1, wherein in step 3), the NKT-like cells are cultured in vitro for 7 to 30 days.

3. The method according to claim 1, wherein in step 3), the NKT-like cells are cultured in vitro for preferably 10 to 27 days.

4. The method according to claim 1, wherein in step 3), the NKT-like cells are cultured in vitro for 14 to 21 days.

5. The method according to claim 1, wherein in step 3), the NKT-like cells are amplified to $1\times10^9 \sim 1\times10^{12}$ cells.

6. The method according to claim 1, wherein in step 3), the NKT-like cells are amplified to $1\times10^{10} \sim 10\times10^{10}$ cells.

7. The method according to claim 1, wherein the cytokine is one selected from the group consisting of GM-CSF, IL-2, IL-4, IL-5, IL-6, IL-7, IL-9, IL-12, IL-15, 4-1BBL and any combination thereof.

8. A preparation method of isolated mammal NKT-like cells, comprising the following steps:
   1) collecting peripheral blood from a mammal subject, separating and removing red blood cells from the peripheral blood;
   2) isolating mononuclear cells from the peripheral blood obtained in step 1) from which red blood cells have been removed, in vitro culturing the isolated mononuclear cells, and adding culture cytokine(s) that stimulate the proliferation and activation of T cell, for a period of time enough to amplify the number of the mononuclear cells by at least 10~1000 times;
   3) sorting the NKT-like cells by using a cell sorting technique with NKT-like cell surface markers; and
   4) harvesting the NKT-like cells obtained in step 3),
   wherein the NKT-like cell surface markers comprise CD8, CD3, TCRαβ, CD161c, CD44, CD62L, CD122, NKG2A/C/E, KLRG1, NKG2D, Ly49G2 and CD27, or comprise CD8, CD3, TCRαβ, CD56, CD44, CD62L, CD122, NKG2A/C/E, KLRG1, NKG2D, Ly49G2 and CD27.

9. The method according to claim 8, wherein in step 2), the mononuclear cells are cultured in vitro for 7 to 30 days.

10. The method according to claim 8, wherein in step 2), the mononuclear cells are cultured in vitro for 10 to 27 days.

11. The method according to claim 8, wherein in step 2), the mononuclear cells are cultured in vitro for 14 to 21 days.

12. The method according to claim 8, wherein in step 2), the mononuclear cells are amplified to $1 \times 10^9 \sim 1 \times 10^{12}$ cells.

13. The method according to claim 8, wherein in step 2), the mononuclear cells are amplified to $1 \times 10^{10} \sim 10 \times 10^{10}$ cells.

14. The method according to claim 8, wherein the cytokine is one selected from the group consisting of GM-CSF, IL-2, IL-4, IL-5, IL-6, IL-7, IL-9, IL-12, IL-15, 4-1BBL and any combination thereof.

\* \* \* \* \*